(12) United States Patent
Wang et al.

(10) Patent No.: US 10,101,299 B2
(45) Date of Patent: Oct. 16, 2018

(54) MAGNETIC SENSOR BASED QUANTITATIVE BINDING KINETICS ANALYSIS

(75) Inventors: Shan X. Wang, Portola Valley, CA (US); Richard S. Gaster, Los Altos, CA (US); Liang Xu, Nanchang (CN); Shu-Jen Han, Cortlandt Manor, NY (US); Robert Wilson, Campbell, CA (US)

(73) Assignee: The Board of Trustees of the Leland Standford Junior University, Palo Alto, CA (US)

( * ) Notice: Subject to any disclaimer, the term of this patent is extended or adjusted under 35 U.S.C. 154(b) by 1389 days.

(21) Appl. No.: 13/046,368

(22) Filed: Mar. 11, 2011

(65) Prior Publication Data
US 2011/0223612 A1 Sep. 15, 2011

Related U.S. Application Data

(60) Provisional application No. 61/313,604, filed on Mar. 12, 2010.

(51) Int. Cl.
G01N 27/00 (2006.01)
G01N 27/74 (2006.01)
G01N 33/557 (2006.01)

(52) U.S. Cl.
CPC ......... *G01N 27/745* (2013.01); *G01N 33/557* (2013.01); *Y10T 436/143333* (2015.01)

(58) Field of Classification Search
USPC ....................................................... 436/526
See application file for complete search history.

(56) References Cited

U.S. PATENT DOCUMENTS

| 5,485,277 A | 1/1996 | Foster |
| 5,981,297 A | 11/1999 | Baselt |
| 6,057,167 A | 5/2000 | Shieh et al. |

(Continued)

FOREIGN PATENT DOCUMENTS

| EP | 2034324 | 3/2009 |
| JP | 2004-167032 A | 6/2004 |

(Continued)

OTHER PUBLICATIONS

Baselt et al. "A Biosensor based on magnetoresistance technology" Oct. 1998, Biosensors and Bioelectronics, vol. 13, Issue 7-8, p. 731-739.*

(Continued)

*Primary Examiner* — Melanie Yu Brown
*Assistant Examiner* — Richard Moerschell
(74) *Attorney, Agent, or Firm* — Rudy J. Ng; Bret E. Field; Bozicevic, Field & Francis LLP

(57) ABSTRACT

Methods for quantitatively determining a binding kinetic parameter of a molecular binding interaction are provided. Aspects of embodiments of the methods include: producing a magnetic sensor device including a magnetic sensor in contact with an assay mixture including a magnetically labeled molecule to produce a detectable molecular binding interaction; obtaining a real-time signal from the magnetic sensor; and quantitatively determining a binding kinetics parameter of the molecular binding interaction from the real-time signal. Also provided are systems and kits configured for use in the methods.

18 Claims, 15 Drawing Sheets

(56) References Cited

U.S. PATENT DOCUMENTS

| | | |
|---|---|---|
| 6,670,115 B1 | 12/2003 | Zhang |
| 6,743,639 B1 | 6/2004 | Tondra et al. |
| 7,048,890 B2 | 5/2006 | Coehoorn et al. |
| 7,238,486 B2 | 7/2007 | Pourmand et al. |
| 7,373,255 B2 | 5/2008 | Karlsson et al. |
| 7,419,639 B2 | 9/2008 | Osterfeld et al. |
| 7,501,253 B2 | 3/2009 | Pourmand et al. |
| 7,504,262 B2 | 3/2009 | Fox |
| 7,615,382 B2 | 11/2009 | Wang et al. |
| 7,682,838 B2 | 3/2010 | Wang et al. |
| 7,766,993 B2 | 8/2010 | Sun et al. |
| 7,906,345 B2 | 3/2011 | Wang et al. |
| 7,939,338 B2 | 5/2011 | Wang et al. |
| 7,977,111 B2 | 7/2011 | Shi et al. |
| 7,989,396 B2 | 8/2011 | Yu et al. |
| 2002/0000398 A1 | 1/2002 | Skold |
| 2002/0081617 A1* | 6/2002 | Buranda et al. ............... 435/6 |
| 2005/0014179 A1 | 1/2005 | Karlsson et al. |
| 2005/0019842 A1 | 1/2005 | Prober et al. |
| 2005/0100930 A1 | 5/2005 | Wang et al. |
| 2005/0131650 A1 | 6/2005 | Andersson et al. |
| 2006/0286685 A1 | 12/2006 | Miller et al. |
| 2007/0207553 A1 | 9/2007 | Fox |
| 2007/0264159 A1* | 11/2007 | Graham ............... G01N 27/745 422/400 |
| 2008/0036450 A1 | 2/2008 | Kahlman et al. |
| 2008/0054896 A1 | 3/2008 | Kahlman et al. |
| 2008/0311598 A1 | 12/2008 | Vossenaar et al. |
| 2008/0318339 A1 | 12/2008 | Vossenaar et al. |
| 2009/0104707 A1 | 4/2009 | Wang et al. |
| 2009/0181464 A1 | 7/2009 | De Theije et al. |
| 2010/0148768 A1 | 6/2010 | Schwarz |
| 2010/0188075 A1 | 7/2010 | Litvinov et al. |
| 2010/0248283 A1 | 9/2010 | Xiao et al. |
| 2010/0289483 A1 | 11/2010 | Immink et al. |
| 2011/0027901 A1 | 2/2011 | Gaster et al. |
| 2011/0151429 A1 | 6/2011 | Haam et al. |
| 2011/0207229 A1* | 8/2011 | Evers ............... B82Y 25/00 436/34 |

FOREIGN PATENT DOCUMENTS

| | | |
|---|---|---|
| JP | 2006184250 | 7/2006 |
| JP | 2008268186 | 11/2008 |
| JP | 2008-546995 | 12/2008 |
| JP | 2009-531023 | 9/2009 |
| WO | 03/031977 | 4/2003 |
| WO | 03/081202 | 10/2003 |
| WO | 06/059270 | 6/2006 |
| WO | 2006/075612 A1 | 7/2006 |
| WO | 2007132374 | 11/2007 |
| WO | 2009/125825 | 10/2009 |

OTHER PUBLICATIONS

Myszka (1998) Biophys J 75: 583-594.*
Osterfeld (2008) PNAS 105: 20637-20640.*
Martins (2009) J Magn and Mag Materials 322: 1655-1663.*
De Boer; et al., "An integrated and sensitive detection platform for magneto-resistive biosensors", Biosensors and Bioelectronics (2007), 22:2366-2370.
Gaster; et al., "Matrix-insensitive protein assays push the limits of biosensors in medicine", Nature Medicine (2009), pp. 1-7.
Mulvaney; et al., "Attomolar protein detection in complex sample matrices with semi-homogeneous fluidic force discrimination assays", Biosensors and Bioelectronics (2009), 24:1109-15.
Osterfeld; et al., "Multiplex protein assays based on real-time magnetic nanotag sensing", PNAS (2008), 105 (52):20637-20640.
Xu; et al., "Giant Magnetoresistive Biochip for DNA Detection and HPV Genotyping", Biosens Bioelectron (2008), 24 (1):99-103.
Martin; et al., "Challenges and trends in the development of a magnetoresistive biochip portable platform", Journal of Magnetism and Magnetic Materials (2010), 322:1655-1663.
Dittmer et al. "Sensitive and rapid immunoassay for parathyroid hormone using magnetic particle labels and magnetic actuation", Journal of Immunological Methods, vol. 338, No. 1-2, Sep. 30, 2008, pp. 40-46.
Hall et al. "GMR Biosensor Arrays: A System Perspective", Biosensors and Bioelectronics, vol. 25, No. 9, Jan. 6, 2010, pp. 2051-2057.

\* cited by examiner

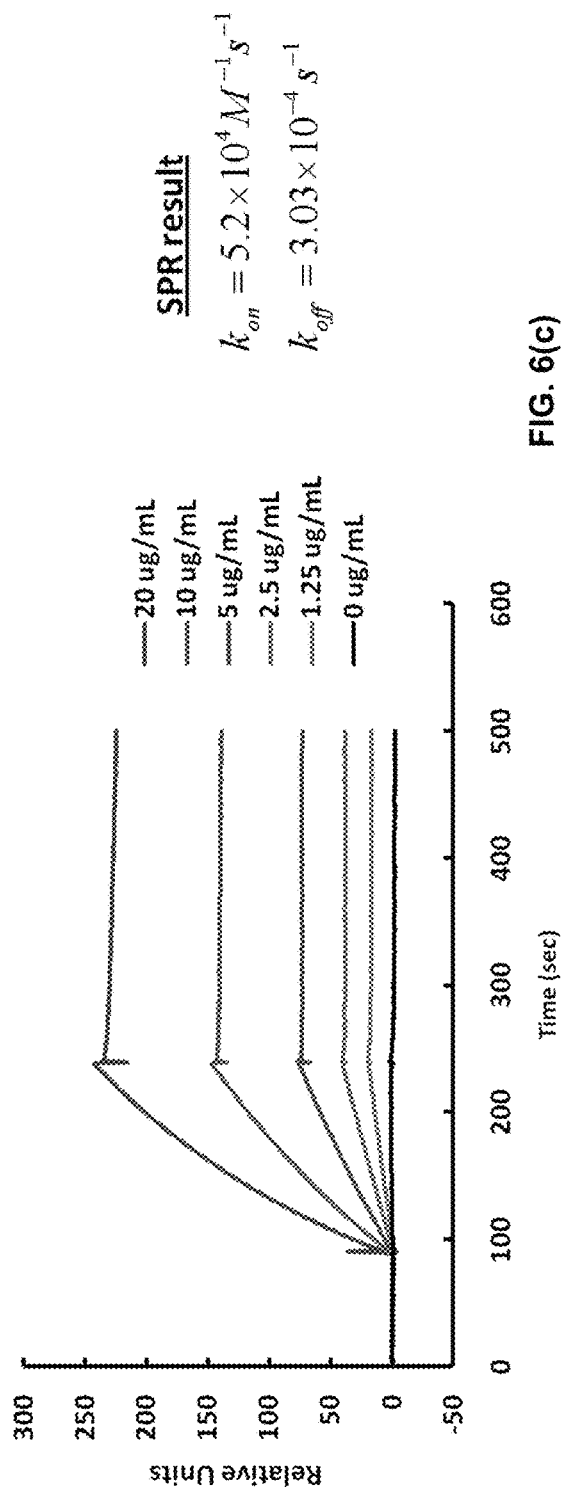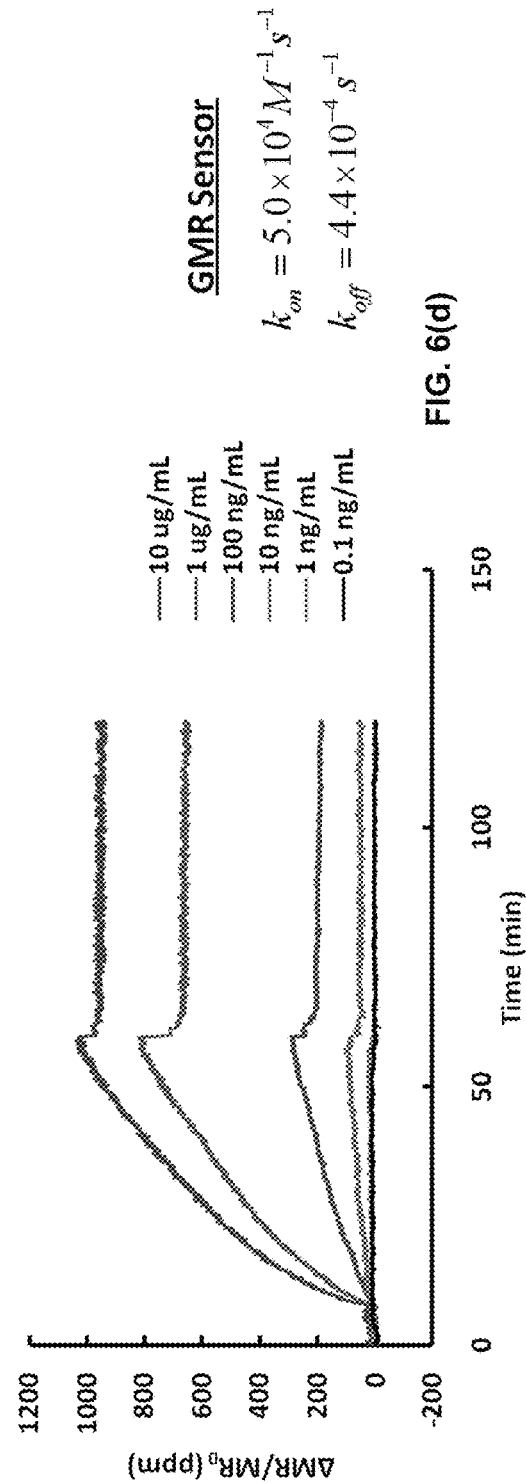
FIG. 6(c)
FIG. 6(d)

FIG. 9(a)
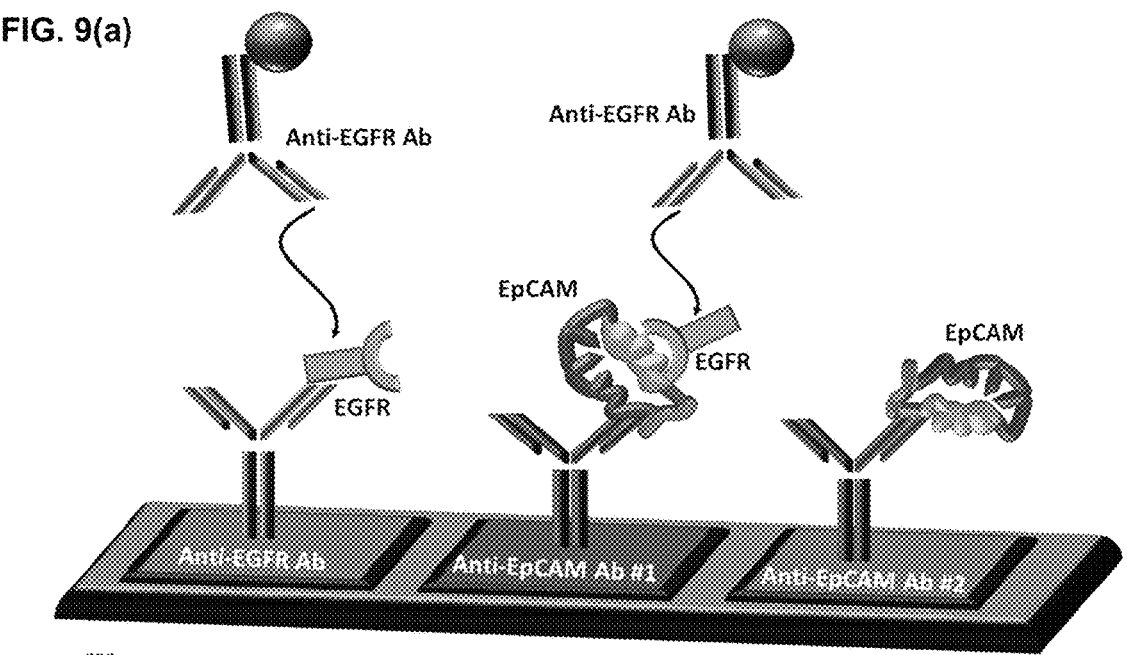
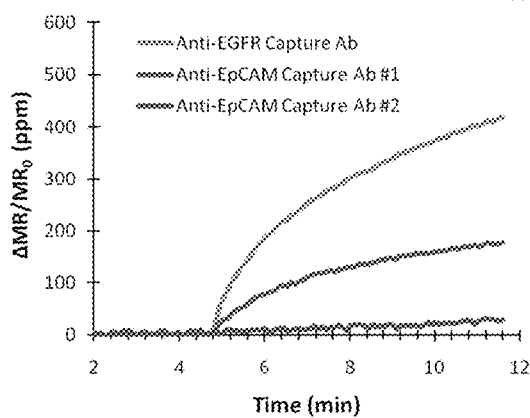
FIG. 9(b)
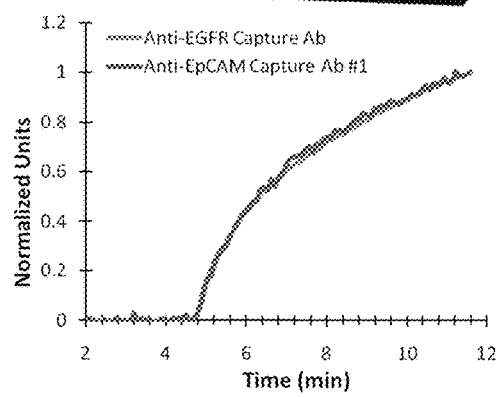
FIG. 9(c)

MAGNETIC SENSOR BASED QUANTITATIVE BINDING KINETICS ANALYSIS

REFERENCE TO RELATED APPLICATION

This application claims the benefit of priority under 35 U.S.C. § 119(e) to U.S. Provisional Patent Application Ser. No. 61/313,604, filed Mar. 12, 2010, the disclosure of which is hereby incorporated by reference in its entirety.

ACKNOWLEDGMENT OF GOVERNMENT SUPPORT

This invention was made with U.S. Government support under Grant No. 1U54CA119367 from National Cancer Institute and Grant No. ECCS-0801385-000 from National Science Foundation. The Government has certain rights in this invention.

INTRODUCTION

Biological processes are dictated by molecular interactions between pairs of first and second molecules. Examples of such molecular interactions include nucleic acid hybridization interactions, protein-protein interactions, protein-nucleic acid interactions, enzyme-substrate interactions and receptor-ligand interactions, e.g., antibody-antigen interactions and receptor-agonist or antagonist interactions.

Affinity-based sensing of DNA hybridization, antigen-antibody binding, and DNA-protein interactions have all been shown to play important roles in basic science research, clinical diagnostics, biomolecular engineering, and drug design. As the state of the art advances, demand for accurate, sensitive, high throughput and rapid methods for determination of molecular identities and reaction details place constant pressure on evolving analytical methods. To meet these pressing needs, researchers have turned to molecular labels in order to improve sensitivity for detection of rare molecules. Such labels, however, can alter diffusion and steric phenomena. In addition, high throughput, or speed requirements often prohibit the use of classical equilibrium methods, so that a detailed understanding of reaction kinetics, diffusion phenomena, and the implications of surface immobilization become vital for the extraction of meaningful reaction parameters.

When evaluating the kinetics of a given molecular interaction, various quantitative kinetic parameters may be of interest. One quantitative kinetic parameter of interest is the association rate constant. The association rate constant (i.e., $k_a$, $k_{on}$) is a mathematical constant describing the bonding affinity of two molecules at equilibrium, such as the bonding affinity of an antibody and an antigen. Another quantitative kinetic parameter of interest is the dissociation rate constant (i.e., $k_d$, $k_{off}$). The dissociation rate constant is a mathematical constant describing the propensity of a larger object to separate (dissociate) reversibly into smaller components, as when a receptor/ligand complex dissociates into its component molecules. A third kinetic parameter of interest is the diffusion rate constant, $k_M$, which is a mathematical constant describing the rate at which labeled molecules diffuse toward a sensor.

SUMMARY

Methods for quantitatively determining a binding kinetic parameter of a molecular binding interaction are provided. Aspects of embodiments of the methods include: producing a magnetic sensor device including a magnetic sensor in contact with an assay mixture including a magnetically labeled molecule to produce a detectable molecular binding interaction; obtaining a real-time signal from the magnetic sensor; and quantitatively determining a binding kinetics parameter of the molecular binding interaction from the real-time signal. Also provided are systems and kits configured for use in the methods.

BRIEF DESCRIPTION OF THE FIGURES

FIG. 6(c) shows a graph of SPR and FIG. 6(d) shows a graph of magnetonanosensor-based platforms that provide similar real-time binding curves when monitoring the kinetics of CEA antibody binding to CEA antigen in parallel experiments, according to embodiments of the present disclosure.

FIG. 9(a) shows a schematic representation of selective protein orientation for epitope mapping and cross reactivity considerations, according to embodiments of the present disclosure. FIG. 9(b) shows a graph for the anti-EGFR Ab sensor, functionalized with anti-EGFR capture antibody (as a control), which captured EGFR and was detected when the anti-EGFR antibody-MNP complex binds, according to embodiments of the present disclosure. FIG. 9(c) shows a graph confirming that the kinetics being monitored was related to the anti-EGFR antibody-MNP complex binding to EGFR, according to embodiments of the present disclosure. The y-axes are presented as changes in MR normalized to the initial MR in parts per million (ppm).

In FIG. 11(a), four groups of four sensors were selectively immobilized with capture antibody to CEA. Each group of sensors that are circled in FIG. 11(a) corresponds to the matching curves in the graph in FIG. 11(b). After washing away the un-reacted capture antibody, detection antibody labeled with MNP tags was incubated in the reaction well.

DETAILED DESCRIPTION

Figure 1:
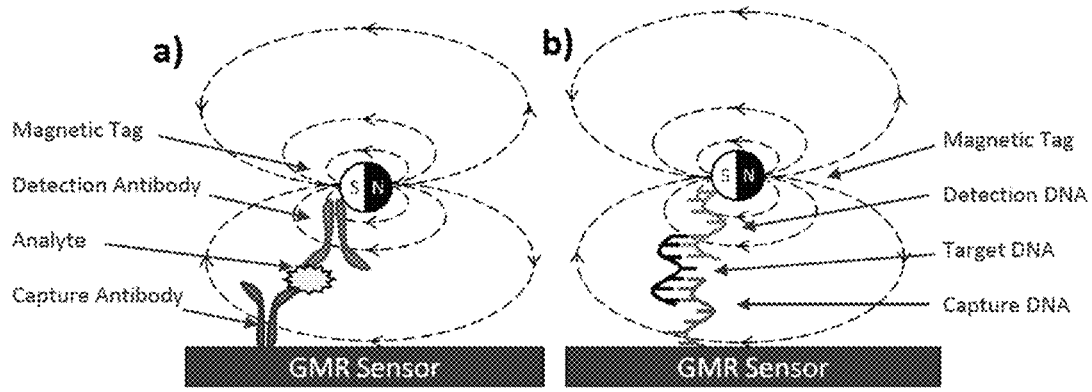
FIG. 1(a) shows a schematic of a sandwich assay with a capture antibody bound to a magnetic sensor, an analyte bound to the capture antibody, and a detection antibody attached to a magnetic tag, according to embodiments of the present disclosure.
FIG. 1(b) shows a schematic of a DNA sandwich assay with a capture DNA bound to a magnetic sensor, a target DNA bound to the capture DNA, and a detection DNA attached to a magnetic tag, according to embodiments of the present disclosure.

Methods for quantitatively determining a binding kinetic parameter of a molecular binding interaction are provided. Aspects of embodiments of the methods include: producing a magnetic sensor device including a magnetic sensor in contact with an assay mixture including a magnetically labeled molecule to produce a detectable molecular binding interaction; obtaining a real-time signal from the magnetic sensor; and quantitatively determining a binding kinetics parameter of the molecular binding interaction from the real-time signal. Also provided are systems and kits configured for use in the methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present invention and are disclosed herein just as if each and every such sub-combination of chemical groups was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing embodiments of the invention, aspects of embodiments of the methods will be described first in greater detail. Next, embodiments of systems and kits that may be used in practicing methods of invention are reviewed.

Methods

As summarized above, embodiments of the invention are directed to methods of quantitatively determining a binding kinetic parameter of a molecular binding interaction of interest. The binding interaction of interest is, in certain embodiments, a binding interaction between a first and second molecule, e.g., between first and second biomolecules. For example, one of the first and second molecules may be a magnetically labeled molecule, and one of the first and second molecules may be a molecule that specifically binds to the magnetically labeled molecule. By "quantitatively determining" is meant expressing the binding kinetic parameter of interest in terms of a quantity, e.g., as a numerical value. By "binding kinetic parameter" is meant a measurable binding kinetic factor that at least partially defines a given molecular interaction and can be employed to define its behavior. Binding kinetic parameters of interest include, but are not limited to, an association rate constant (i.e., $k_a$, $k_{on}$), a dissociation rate constant (i.e., $k_d$, $k_{off}$), a diffusion-limited rate constant (i.e., $k_M$), an activation energy (i.e., $E_A$), transport parameters such as diffusivity, etc.

As summarized above, methods of the invention may include the following steps:
1) producing a magnetic sensor device in contact with an assay mixture that includes a magnetically labeled molecule;
2) obtaining a real-time signal from a magnetic sensor device; and
3) quantitatively determining a binding kinetic parameter of a molecular binding interaction from the real-time signal.

Each of these steps will now be described in greater detail. Producing a Magnetic Sensor Device in Contact with an Assay Mixture that Includes a Magnetically Labeled Molecule Aspects of the methods include producing a magnetic sensor device in contact with an assay mixture that includes a magnetically labeled molecule. The methods include producing a device or construct in which a magnetic sensor is contacted with a composition (e.g., an assay mixture) that includes the member molecules of a binding interaction of interest (i.e., the binding pair members of the binding interaction of interest) and a magnetic label, where the magnetic label may be a moiety or domain of one of the member molecules of the binding interaction of interest, or a component of a distinct molecule, e.g., a third molecule that specifically binds to one of the two member molecules of the binding interaction of interest. In the composition or assay mixture contacting the magnetic sensor, the magnetic label may be stably associated, e.g., either covalently or non-covalently, with one of the binding pair members to produce a magnetically labeled molecule. As will be further described below, the step of producing a magnetic sensor device in contact with an assay mixture that includes a magnetically labeled molecule may include a variety of different process subcombinations, e.g., in terms of when the binding pair members are contacted with each other, and or the magnetic sensor, the configuration of the binding pair members relative to the device, etc.

Binding Pairs

A given binding interaction to be quantitatively kinetically analyzed according to methods as described herein may be made up of a binding pair of molecules, such as a first and second biomolecule. The binding pair of molecules may vary widely depending on the binding interaction of interest. Binding interactions of interest include any interaction between the binding pair of molecules, where the binding interaction occurs with specificity between the binding pair of molecules under the environmental conditions of the binding interaction. Examples of binding interactions of interest include, but are not limited to: nucleic acid hybridization interactions, protein-protein interactions, protein-nucleic acid interactions, enzyme-substrate interactions and receptor-ligand interactions, e.g., antibody-antigen interactions and receptor-agonist or antagonist interactions.

Examples of molecules that have molecular binding interactions of interest include, but are not limited to: biopolymers and small molecules, which may be organic or inorganic small molecules. A "biopolymer" is a polymer of one or more types of repeating units. Biopolymers may be found in biological systems (although they may be made synthetically) and may include peptides, polynucleotides, and polysaccharides, as well as such compounds composed of or containing amino acid analogs or non-amino acid groups, or nucleotide analogs or non-nucleotide groups. As such, biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. For example, a "biopolymer" may include DNA (including cDNA), RNA, oligonucleotides, and PNA and other polynucleotides as described in U.S. Pat. No. 5,948,902 and references cited therein. A "biomonomer" references a single unit, which can be linked with the same or other biomonomers to form a biopolymer (e.g., a single amino acid or nucleotide with two linking groups, one or both of which may have removable protecting groups).

The term "peptide" as used herein refers to any polymer compound produced by amide formation between an α-carboxyl group of one amino acid and an α-amino group of another group. The term "oligopeptide" as used herein refers to peptides with fewer than about 10 to 20 residues, i.e. amino acid monomeric units. The term "polypeptide" as used herein refers to peptides with more than 10 to 20 residues. The term "protein" as used herein refers to polypeptides of specific sequence of more than about 50 residues and includes D and L forms, modified forms, etc. The terms "polypeptide" and "protein" may be used interchangeably.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Nucleic acids can be of any length, e.g., 2 bases or longer, 10 bases or longer, 100 bases or longer, 500 bases or longer, 1000 bases or longer, including 10,000 bases or longer. The term "polynucleotide" as used herein refers to single- or double-stranded polymers composed of nucleotide monomers of generally greater than about 100 nucleotides in length. Polynucleotides include single or multiple stranded configurations, where one or more of the strands may or may not be completely aligned with another. The terms "ribonucleic acid" and "RNA" as used herein mean a polymer composed of ribonucleotides. The terms "deoxyribonucleic acid" and "DNA" as used herein mean a polymer composed of deoxyribonucleotides. The term "oligonucleotide" as used herein denotes single-stranded nucleotide multimers of from about 10 to about 200 nucleotides in length, such as from about 25 to about 175 nucleotides in length, including from about 50 to about 160 nucleotides in length, e.g., 150 nucleotides in length.

In some instances, the binding pair of molecules are ligands and receptors, where a given receptor or ligand may or may not be a biopolymer. The term "ligand" as used herein refers to a moiety that is capable of covalently or otherwise chemically binding a compound of interest. Ligands may be naturally-occurring or manmade. Examples of ligands include, but are not restricted to, agonists and antagonists for cell membrane receptors, toxins and venoms, viral epitopes, hormones, opiates, steroids, peptides, enzyme substrates, cofactors, drugs, lectins, sugars, oligonucleotides, nucleic acids, oligosaccharides, proteins, and the like.

The term "receptor" as used herein is a moiety that has an affinity for a ligand. Receptors may be naturally-occurring or manmade. They may be employed in their unaltered state or as aggregates with other species. Receptors may be attached, covalently or noncovalently, to a binding member, either directly or via a specific binding substance. Examples of receptors include, but are not restricted to, antibodies, cell membrane receptors, monoclonal antibodies and antisera reactive with specific antigenic determinants, viruses, cells, drugs, polynucleotides, nucleic acids, peptides, cofactors, lectins, sugars, polysaccharides, cellular membranes, organelles, and the like. Receptors are sometimes referred to in the art as anti-ligands. As the term receptor is used herein, no difference in meaning is intended. A "Ligand Receptor Pair" is formed when two molecules have combined through molecular recognition to form a complex.

Magnetic Sensor Devices

Magnetic sensor devices of interest are those which generate an electrical signal in response to a magnetic label associating with a surface of the sensor. Magnetic sensor devices of interest include, but are not limited to, magnetoresistance sensor devices, including giant magnetoresistance (GMR) devices. GMR devices of interest include, but are not limited to spin valve detectors, and magnetic tunnel junction (MTJ) detectors.

Spin-Valve Detectors

In some instances, the magnetic sensor is a spin valve detector. A spin valve detector is a metallic multilayer thin-film structure of two ferromagnetic layers spaced by a non-magnetic layer, e.g., copper. One ferromagnetic layer, called the pinned layer, has its magnetization pinned to a certain direction, while the magnetization of the other ferromagnetic layer, called the free layer, can rotate freely under an applied magnetic field. The electrical resistance of a spin valve depends on the relative orientation of magnetization of the free layer to that of the pinned layer. When the two magnetizations are parallel, the resistance is the lowest; when antiparallel, the resistance is the highest. The relative change of resistance is called the magnetoresistance (MR) ratio. In some cases, the MR ratio of a spin valve can reach more than about 10% in a small magnetic field, e.g., about 100 Oe. Therefore, a spin valve can function as a sense element for the detection of magnetically labeled molecule associate with the sensor surface.

In certain embodiments, spin valves have a magnetoresistive (MR) ratio of about 1% to about 20%, such as about 3% to about 15%, including about 5% to about 12%. Therefore, in certain embodiments, spin vales can detect a single magnetic label of about 10 nm size in a narrow bandwidth (i.e., about 1 Hz or less) or with lock-in detection. In these cases, by narrowing the noise bandwidth, a sufficient signal to noise ratio (SNR) is achieved even for single nanoparticle detection.

Spin valve detection may be performed with the in-plane mode (see e.g., Li, et al., *J. Appl. Phys.*, vol. 93 (10): 7557 (2003)). In other embodiments, the vertical mode can be used when the electromagnetic interference (EMI) signal due to the AC tickling field in the detection system is detectable. The EMI signal tends to center at the frequency, f, of the AC tickling field, so it can be substantially eliminated or reduced by performing lock-in detection at the frequency 2f. Furthermore, in some instances, a 2-bridge circuit can be used to substantially remove the remaining EMI. Other signal acquisition and processing methods with an AC modulation sense current and an AC tickling field at two different frequencies may be used (e.g., S-J Han, H. Yu, B. Murmann, N. Pourmand, and S. X. Wang, *IEEE International Solid-State Circuits Conference (ISSCC) Dig. Tech. Papers*, San Francisco Marriott, CA, USA, Feb. 11-15, 2007.)

In certain embodiments, the signal from the spin valve detector due to the magnetic label depends on the distance between the magnetic label and the free layer of the spin valve, in addition to the geometry and bias field of the spin valve itself. The detector voltage signal from a single magnetic label decreases with increasing distance from the center of the particle to the mid-plane of the spin valve free layer.

In certain embodiments, the free layer in the spin valve is on top of the pinned layer to facilitate detection of the magnetic label because the sensing magnetic field from a magnetic particle drops monotonically with the distance between the sensor and the particle. Minimization of the distance between the magnetic label and the top surface of the free layer, including the thickness of the passivation layer protecting the spin valve, may facilitate magnetic particle detection.

In certain embodiments, the spin-valve sensor may include a passivation layer on one or more of the detector surfaces. In some embodiments, the detector combines a thin (e.g., 60 nm or less, such as 50 nm or less, including 40 nm or less, 30 nm or less, 20 nm or less, or 10 nm or less) layer of passivation (e.g., in those embodiments where the detector is employed with magnetic nanoparticle tags with a mean diameter of 50 nm or less. In certain embodiments, larger, micron-sized magnetic particles are employed. In some instances, the thin layers of passivation suitable for use with the presently disclosed detectors can have a thickness from about 1 nm to about 10 nm, such as from about 1 nm to about 5 nm, including from about 1 nm to about 3 nm. In certain embodiments, the thin layers of passivation suitable for use with the presently disclosed detectors can have a thickness from about 10 nm to about 50 nm, such as from about 20 nm to about 40 nm, including from about 25 nm to about 35 nm. The passivation layers may include, but are not limited to, Ta, Au, or oxides thereof, combinations thereof, and the like.

Further details regarding spin valve detectors and protocols for their use are provided in United States Patent Publication Nos. 2005/0100930 and 2009/0104707; the disclosures of which are herein incorporated by reference.

Magnetic Tunnel Junction Detectors

In certain embodiments, the magnetic sensors are magnetic tunnel junction (MTJ) detectors. An MTJ detector is constructed similarly to a spin valve detector except that the non-magnetic spacer is replaced with an insulating layer (e.g., an insulating tunnel barrier), such as alumina or MgO, through which the sense current flows perpendicular to the film plane. Electron tunneling between two ferromagnetic electrodes is controlled by the relative magnetization of the two ferromagnetic electrodes, i.e., the tunneling current is high when they are parallel and low when antiparallel. In certain embodiments, the MTJ detector includes a bottom electrode, magnetic multilayers disposed on either side of the tunnel barrier, and a top electrode. In some cases, MTJ detectors have magnetoresistance ratios exceeding 200% (S. Ikeda, J. Hayakawa, Y. M. Lee, F. Matsukura, Y. Ohno, T. Hanyu, and H. Ohno, *IEEE Transactions on Electron Devices*, vol. 54, no. 5, 991-1001 (2007)) and large device resistances, yielding higher output voltage signals.

In certain embodiments, the MTJ detector has a double-layer top electrode. The first layer can be a metallic layer (e.g., gold layer) wherein the layer may have a thickness in some instances of 60 nm or less, such as 50 nm or less, including 40 nm or less, 30 nm or less, 20 nm or less, or 10 nm or less. The second layer can be a conductive metal, e.g., copper, aluminum, palladium, palladium alloys, palladium oxides, platinum, platinum alloys, platinum oxides, ruthenium, ruthenium alloys, ruthenium oxides, silver, silver alloys, silver oxides, tin, tin alloys, tin oxides, titanium, titanium alloys, titanium oxides, combinations thereof, and the like. In some instances, an aperture in the second layer is slightly smaller in size than the MTJ. In certain embodiments, the sensor is configured so that, during use, the distance between an associated magnetic label and the top surface of the free magnetic layer ranges from 5 nm to 100 nm, such as from 5 nm to 50 nm, including from 5 nm to 30 nm, such as from 5 nm to 20 nm, including from 5 nm to 10 nm. In some instances, this arrangement facilitates the reduction or substantial prevention of current crowding (see e.g., van de Veerdonk, R. J. M., et al., *Appl. Phys. Lett.*, 71: 2839 (1997)) within the top electrode which may occur if only a thin gold electrode is used.

Except that the sense current flows perpendicular to the film plane, the MTJ detector can operate similarly to the spin valve detector, either with in-plane mode or vertical mode of the applied modulation field. As discussed above regarding spin valve detectors, in certain embodiments, the vertical mode of the applied modulation field can be used for reducing EMI and, similarly, thin passivation also applies to MTJ detectors. In addition, the first top electrode of thin gold on MTJ detectors can also facilitate electrical conduction, passivation, and specific biomolecular probe attachment.

In certain embodiments, at the same detector width and particle-detector distance, MTJ detectors can give larger signals than spin valve detectors. For example, for an MTJ detector with a junction area of 0.2 μm by 0.2 μm and resistance-area product of 1 kOhm-μm$^2$, operating with a MR of 250% at a bias voltage of 250 mV, and $H_b$=35 Oe, $H_t$=100 Oe rms, the voltage signal from a single 11 nm diameter Co nanoparticle whose center is 35 nm away from the midplane of the free layer may be about 200 μV. In some instances, this voltage is an order of magnitude, or more, greater than the voltage for similar-sized spin valve detectors.

Further details regarding MTJ detectors and protocols for their use are provided in United States Patent Publication Nos. 2005/0100930 and 2009/0104707, the disclosures of which are herein incorporated by reference.

Magnetic Sensor Device Configurations

The magnetic sensor devices may have a variety of different configurations, e.g., with respect to sensor configuration, whether the devices are configured for batch or flow through use, etc. As such, any configuration that provides a magnetic sensor of the device to come into contact with a mixture of the binding members of the molecular binding interaction of interest and the magnetic label may be employed. Accordingly, configurations of the magnetic sensor device may include, but are not limited to: well configurations (in which the sensor is associated with the bottom or walls of a fluid containment structure, such as a well); flow through configurations, e.g., where the sensor is associated with a wall of a flow cell having a fluid input and output; etc.

In certain embodiments, the subject magnetic sensor device includes a substrate surface which displays two or more distinct magnetic sensors on the substrate surface. In certain embodiments, the magnetic sensor device includes a substrate surface with an array of magnetic sensors.

An "array" includes any two-dimensional or substantially two-dimensional (as well as a three-dimensional) arrangement of addressable regions, e.g., spatially addressable regions. An array is "addressable" when it has multiple sensors positioned at particular predetermined locations (i.e., "addresses") on the array. Array features (i.e., sensors) may be separated by intervening spaces. Any given substrate may carry one, two, four or more arrays disposed on a front surface of the substrate. Depending upon the use, any or all of the arrays may sense targets which are the same or different from one another and each may contain multiple distinct magnetic sensors. An array may contain one or more, including two or more, four or more, 8 or more, 10 or more, 50 or more, or 100 or more, 1000 or more, 10,000 or more, or 100,000 or more magnetic sensors. For example, 64 magnetic sensors can be arranged into an 8×8 array. In certain embodiments, the magnetic sensors can be arranged into an array with an area of 10 cm$^2$ or less, or 5 cm$^2$ or less, e.g., 1 cm$^2$ or less, including 50 mm$^2$ or less, 20 mm$^2$ or less, such as 10 mm$^2$ or less, or even smaller. For example, magnetic sensors may have dimensions in the range of 10 μm×10 μm to 200 μm×200 μm, including dimensions of 100 μm×100 μm or less, such as 90 μm×90 μm or less, for instance 50 μm×50 μm or less.

In certain embodiments, the magnetic sensor may include a plurality of linear magnetoresistive segments. For instance, the magnetic sensor can include 4 or more, such as 8 or more, including 12 or more, or 16 or more, e.g. 32 or more, for example 64 or more, or 72 or more, or 128 or more linear magnetoresistive segments. The magnetoresistive segments can each be 1000 nm wide or less, such as 750 nm wide or less, or 500 nm wide or less, for instance 250 nm wide or less. In some cases, the magnetoresistive segments can each be 50 nm thick or less, such as 40 nm thick or less, including 30 nm thick or less, or 20 nm thick or less, for example 10 nm thick or less. The magnetoresistive segments can each be 1000 nm long or less, or 750 nm long or less, or 500 nm long or less, or 250 nm long or less, for example 100 nm long or less, or 50 nm long or less.

Figure 12:
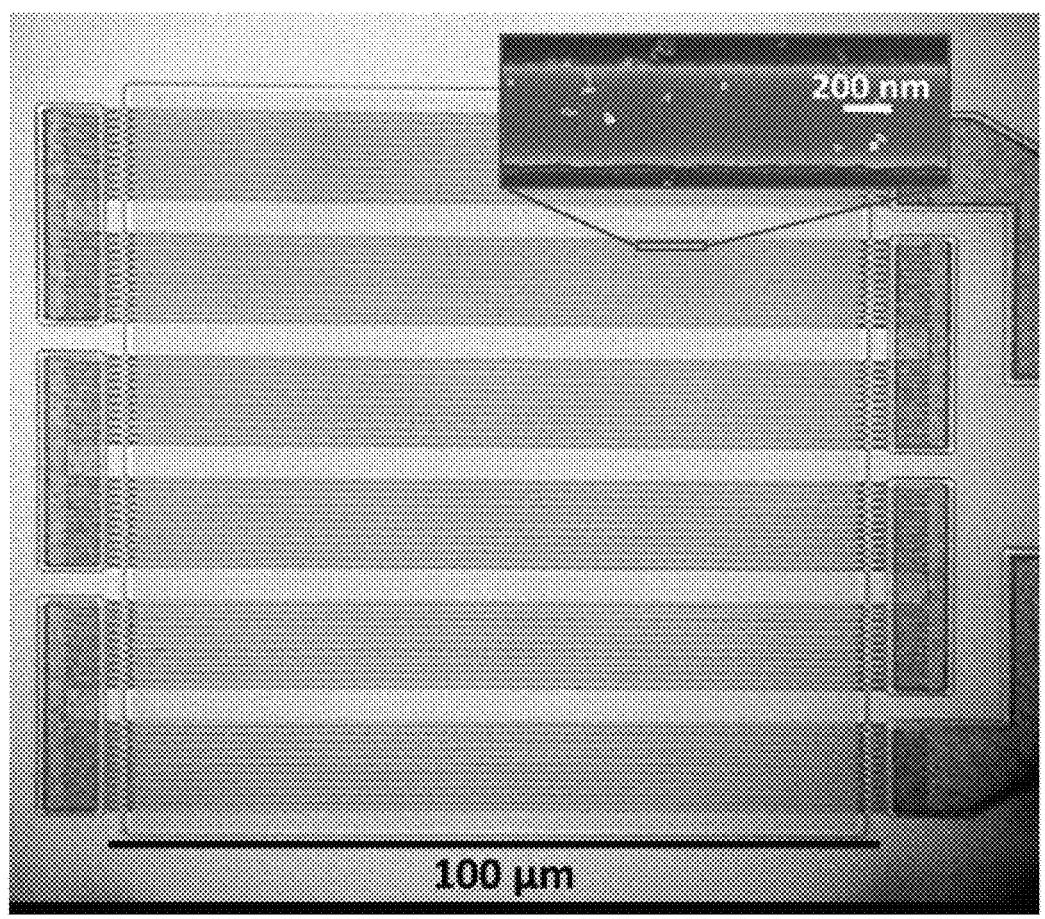
FIG. 12 shows an optical microscopy image of a GMR sensor architecture including 72 magnetic sensor stripes connected in parallel and in series. The insert in FIG. 12 shows a scanning electron microscope (SEM) image of one magnetic sensor stripe of the GMR sensor with several bound magnetic nanoparticle tags.

The magnetoresistive segments may be connected together in series, or the magnetoresistive segments may be connected together in parallel. In certain instances, the magnetoresistive segments are connected together in series and in parallel. In these instances, two or more magnetoresistive segments may be connected together in parallel, and two or more groups of these parallel-connected magnetoresistive segments may be connected together in series. An example of a magnetic sensor that includes magnetoresistive segments connected together in parallel and in series is shown in FIG. 12.

In certain embodiments, at least some, or all, of the magnetic sensor or sensors of a given device have a binding pair member stably associated with a surface of the sensor. The binding pair member may vary, depending on the nature of the particular assay being performed. As such, the binding pair member may be a capture probe that specifically binds to a molecule of the molecular binding interaction of interest, or a molecule that participates in the molecular binding interaction of interest, e.g., a molecule that specifically binds to the magnetically labeled molecule. By "stably associated" is meant that the binding pair member and sensor surface maintain their position relative to each other in space for greater than a transient period of time under the conditions of use, e.g., under the assay conditions. As such, the binding pair member and sensor surface can be non-covalently or covalently stably associated with each other. Examples of non-covalent association include non-specific adsorption, binding based on electrostatic (e.g. ion, ion pair interactions), hydrophobic interactions, hydrogen bonding interactions, specific binding through a specific binding pair member covalently attached to the support surface, and the like. Examples of covalent binding include covalent bonds formed between binding pair member and a functional group present on the sensor surface, e.g. —OH, where the functional group may be naturally occurring or present as a member of an introduced linking group. Accordingly, the binding pair member may be adsorbed, physisorbed, chemisorbed, or covalently attached to the magnetic sensor surface.

Where a given device includes two or more magnetic sensors, each sensor may have the same or different binding pair member associated with its surface. Accordingly, different capture probes or molecules that bind to the magnetically labeled molecule may be present on the sensor surfaces of such devices, such that each magnetic sensor specifically binds to a distinct molecule. Such devices may also include sensors that are free of any binding pair member (e.g., where such blank sensors may serve as sources of reference or control electrical signals).

In multi-sensor devices, areas in between the magnetic sensors may be present which do not carry any analyte specific probes. Such inter-sensor areas, when present, may be of various sizes and configurations. In some instances, these inter-sensor areas may be configured to reduce or prevent fluid movement among different sensors, e.g., where the inter-sensor areas include hydrophobic materials and/or fluid barriers (such as walls).

In certain embodiments, the substrate of the device, e.g., which may carry one or more arrays of distinct sensors, is shaped generally as a rectangular solid (although other shapes are possible), having a length of 1 mm or more and 150 mm or less, such as 1 mm or more and 100 mm or less, for instance 50 mm or less, or 10 mm or less; a width of 1 mm or more and 150 mm or less, such as 100 mm or less, including 50 mm or less, or 10 mm or less; and a thickness of 0.01 mm or more and 5.0 mm or less, such as 0.1 mm or more and 2 mm or less, including 0.2 mm or more and 1.5 mm or less, for instance 0.5 mm or more and 1.5 mm or less.

Electronic communication elements, e.g., conductive leads, may be present which are configured to electronically couple the sensor or sensors to "off-chip" components, such as device components, e.g., processors, displays, etc.

As described in greater detail below, a given magnetic sensor device may include a variety of components in addition to the sensor structure (e.g., array), such as described above. Additional device components may include, but are not limited to: signal processing components, data display components (e.g., graphical user interfaces); data input and output devices, power sources, fluid handling components, etc.

Magnetic Labels

In embodiments of the methods, any convenient magnetic label may be employed. Magnetic labels are labeling moieties that, when sufficiently associated with a magnetic sensor, are detectable by the magnetic sensor and cause the magnetic sensor to output a signal. Magnetic labels of interest may be sufficiently associated with a magnetic sensor if the distance between the center of the label and the surface of the sensor is 200 nm or less, such as 100 nm or less, including 50 nm or less.

In certain embodiments, the magnetic labels are nanoparticles. Nanoparticles useful in the practice of certain embodiments are magnetic (e.g., ferromagnetic) colloidal materials and particles. The magnetic nanoparticles can be high moment magnetic nanoparticles which may be super-paramagnetic, or synthetic anti-ferromagnetic nanoparticles which include two or more layers of anti-ferromagnetically-coupled high moment ferromagnets. Both of these types of nanoparticles appear "nonmagnetic" in the absence of a magnetic field, and do not substantially agglomerate. In accordance with certain embodiments, magnetizable nanoparticles suitable for use include one or more materials such as, but not limited to, paramagnetic, super-paramagnetic, ferromagnetic, and ferri-magnetic materials, as well as combinations thereof.

In certain embodiments, the magnetic nanoparticles (also referred to as magnetic tags herein) have remnant magnetizations that are small, such that they will not agglomerate in solution. Examples of magnetic nanoparticles that have small remnant magnetizations include super-paramagnetic particles and anti-ferromagnetic particles. In certain cases, the magnetic tags have detectable magnetic moments under a magnetic field of about 100 Oe. In some instances, the size of the magnetic tags is comparable to the size of the target biomolecules so that the magnetic tags do not interfere with binding interactions between the molecules of interest. In certain embodiments, the magnetic tags are substantially uniform in shape and chemically stable in a biological environment, which may facilitate their use in the assay conditions. In some cases, the magnetic tags are biocompatible, i.e., water soluble and functionalized so that they may be readily attached to biomolecules of interest, e.g., a receptor that specifically binds to a target analyte.

In certain embodiments, the magnetic nanoparticles are high moment magnetic nanoparticles such as Co, Fe or CoFe nanocrystals, which may be super-paramagnetic at room temperature. The magnetic nanoparticles can be fabricated by chemical routes such as, but not limited to, salt reduction or compound decomposition in appropriate solutions. Examples of such magnetic nanoparticles include, but are not limited to, those described by S. Sun, and C. B. Murray, *J. Appl. Phys.*, 85: 4325 (1999); C. B. Murray, et al., *MRS Bulletin*, 26: 985 (2001); and S. Sun, H. Zeng, D. B. Robinson, S. Raoux, P. M. Rice, S. X. Wang, and G. Li, *J. Am. Chem. Soc.*, 126, 273-279 (2004).). In certain embodiments, the magnetic nanoparticles particles can be synthesized with controlled size (e.g., about 5-12 nm), are monodisperse, and are stabilized with oleic acid. Magnetic nanoparticles suitable for use herein include, but are not limited to, Co, Co alloys, ferrites, cobalt nitride, cobalt oxide, Co—Pd, Co—Pt, iron, iron alloys, Fe—Au, Fe—Cr, Fe—N, $Fe_3O_4$, Fe—Pd, Fe—Pt, Fe—Zr—Nb—B, Mn—N, Nd—Fe—B, Nd—Fe—B—Nb—Cu, Ni, Ni alloys, and the like. In some embodiments, a thin layer of gold is plated onto a magnetic core, or a poly-L-lysine coated glass surface can be attached to a magnetic core. Suitable nanoparticles are commercially available from, e.g., Nanoprobes, Inc. (Northbrook, Ill.), and Reade Advanced Materials (Providence, R.I.).

In some cases, magnetic nanoparticle tags are fabricated by physical methods (see e.g., W. Hu, R. J. Wilson, A. Koh, A. Fu, A. Z. Faranesh, C. M. Earhart, S. J. Osterfeld, S.-J. Han, L. Xu, S. Guccione, R. Sinclair, and S. X. Wang, *Advanced Materials*, 20, 1479-1483 (2008)) instead of chemical routes, and are suitable for labeling the target biomolecules to be detected. The magnetic tags may include two or more ferromagnetic layers, such as $Fe_xCo_{1-x}$, where x is 0.5 to 0.7, or $Fe_xCo_{1-x}$ based alloys. In some cases, $Fe_xCo_{1-x}$ has a saturation magnetization of 24.5 kGauss. These ferromagnetic layers may be separated by nonmagnetic spacer layers such as Ru, Cr, Au, etc., or alloys thereof. In certain cases, the spacer layers include ferromagnetic layers coupled antiferromagnetically so that the net remnant magnetization of the resulting particles are zero or near zero. In certain embodiments, the antiferromagnetic coupling can be achieved via RKKY exchange interaction (see e.g., S. S. P. Parkin, et al., *Phys. Rev. Lett.*, 64(19): 2304 (1990)) and magnetostatic interaction (J. C. Slonczewski, et al., *IEEE Trans. Magn.*, 24(3): 2045 (1988)). In some cases, the antiferromagnetic coupling strength is such that the particles can be saturated (i.e., magnetization of all layers become parallel) by an external magnetic field of 100 Oe. In some cases, the antiferromagnetic coupling strength depends of the layer thicknesses and the alloy composition of the spacer layer.

In particular embodiments, to facilitate the bio-conjugation of the nanoparticle, a gold cap (or cap of functionally analogous or equivalent material) is layered on the top of the layers of anti-ferromagnetic material so that the nanoparticle can be conjugated to biomolecules via a gold-thiol or other convenient linkage. Surfactants may be applied to the nanoparticles, such that the nanoparticles may be water-soluble. The edges of the nanoparticles can also be passivated with Au or other inert layers for chemical stability.

Any convenient protocol may be employed to fabricate the nanoparticles described above. For instance, the layers of the nanoparticles can include nanometer-scale ferromagnetic and spacer layers deposited on substrates or release layers with substantially smooth surfaces. In some instances, a mask layer can be formed by imprinting, etching, self assembly, etc. Subsequently, the mask layer and other unwanted layers may be removed and cleaned off thoroughly. Then, the release layer may be removed, lifting off nanoparticles which are the negative image of the mask layer. The particles may then be contacted with surfactants and biomolecules. In some cases, the substrate can be reused after thorough cleaning and chemical mechanical polishing (CMP).

In other embodiments, the nanoparticles are fabricated with a subtractive fabrication method. In this case, the layers are directly deposited on the release layer followed by a mask layer. The layers are etched through the mask layer, and eventually released from the substrate. These nanoparticles result from a positive image of the mask layer as opposed to the case in the additive fabrication method.

In certain embodiments, the size of the magnetic nanoparticles suitable for use with the present invention is comparable to the size of the biomolecules of the molecular binding interaction of interest, such that the nanoparticles do not interfere with the binding interaction of interest. Consequently, the size of the magnetic nanoparticles is, in some embodiments, sub-micron sized, e.g., from 5 nm to 250 nm (mean diameter), such as from 5 nm to 150 nm, including from 5 nm to 20 nm. For example, magnetic nanoparticles having a mean diameter of 5 nm, 6 nm, 7 nm, 8, nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 55 nm, 60 nm, 70 nm, 80 nm, 90 nm, 100 nm, 110 nm, 120 nm, 130 nm, 140 nm, 150 nm, and 300 nm as well as nanoparticles having mean diameters in ranges between any two of these values, are suitable for use herein. Further, in addition to a spherical shape, magnetic nanoparticles suitable for use herein can be shaped as disks, rods, coils, fibers, and the like.

In some embodiments, the magnetic labels are colloidally stable, e.g., nanoparticle compositions may be present as a stable colloid. By colloidally stable is meant that the nanoparticles are evenly dispersed in solution, such that the nanoparticles do not substantially agglomerate. In certain embodiments, to prevent clumping, the nanoparticles may have no net magnetic moment (or a very small magnetic moment) in zero applied field. Anti-ferromagnetic particles may have zero magnetic moment in zero field at all sizes. In contrast, for a ferromagnetic particle, its size may be below the "super-paramagnetic limit", which is, in some cases, about 20 nm or less, such as about 15 nm or less, including about 10 nm or less.

In certain embodiments, the synthetic nanoparticles can be produced in large quantities using a large wafer and standard vacuum thin film deposition processes. For example, with a 6-inch round wafer, 30-nm diameter nanoparticles at a rate of approximately $5 \times 10^{12}$ particles per run can be produced, assuming each particle occupies a square of 60 nm by 60 nm on the wafer.

In some instances, a molecule of a given binding interaction of interest and the magnetic label are stably associated with each other. By "stably associated" is meant that the biomolecule and the magnetic label maintain their position relative to each other in space for greater than a transient period of time under the conditions of use, e.g., under the assay conditions. As such, the biomolecule and magnetic label can be non-covalently or covalently stably associated with each other. Examples of non-covalent association include non-specific adsorption, binding based on electrostatic (e.g. ion, ion pair interactions), hydrophobic interactions, hydrogen bonding interactions, specific binding through a specific binding pair member covalently attached to the support surface, and the like. Examples of covalent binding include covalent bonds formed between the biomolecule and a functional group present on the surface of the label, e.g. —OH, where the functional group may be naturally occurring or present as a member of an introduced linking group.

Assay Mixture Production

The magnetic sensor device which includes a magnetic sensor in contact with an assay mixture that includes a magnetically labeled molecule may be produced using any number of different protocols. For example, a first molecule that specifically binds to the magnetically labeled molecule may be bound to a capture probe on the sensor surface, and then subsequently contacted with the magnetically labeled molecule (e.g., a second biomolecule which may be magnetically labeled). In these instances, methods may include providing a magnetic sensor device having a magnetic sensor which displays a capture probe that specifically binds to the first molecule, which also specifically binds to the magnetically labeled molecule; and then contacting the magnetic sensor with the first molecule and the magnetically labeled molecule. The contacting may include sequentially applying the first molecule, which binds to the surface and is capable of specific binding to the magnetically labeled molecule, and then applying the magnetically labeled molecule to the magnetic sensor.

Alternatively, the first molecule that specifically binds to the magnetically labeled molecule and the magnetically labeled molecule may be combined prior to contact with the sensor to form a complex, and the resultant complex may be allowed to bind to the capture probe on the sensor (e.g., where the binding kinetics of the binding interaction between the first molecule and the capture probe are of interest). In these instances, the contacting includes producing a reaction mixture that includes the first molecule that specifically binds to the magnetically labeled molecule and the magnetically labeled molecule, and then applying the reaction mixture to the magnetic sensor.

In yet other embodiments, the first molecule that specifically binds to the magnetically labeled molecule is first positioned on the sensor, and then contacted with the magnetically labeled second molecule. In these instances, the methods include providing a magnetic sensor device having a magnetic sensor which displays the first molecule (without an intervening capture probe); and then contacting the magnetic sensor with the magnetically labeled molecule.

FIGS. 1(a) and 1(b) provide schematic illustrations for assay protocols that may be employed in the quantitative analysis of the binding kinetics of an antibody/analyte interaction and a nucleic acid hybridization interaction, respectively. In FIG. 1(a), the protocol which is employed is a sandwich assay protocol in which a capture antibody stably associated with the GMR sensor surface is bound to an analyte which in turn is bound to a detection antibody attached to a magnetic tag. In FIG. 1(b), the protocol employed is a DNA sandwich assay in which a capture DNA is associated with the GMR sensor surface, a target DNA is hybridized to the capture DNA, and a detection DNA attached to a magnetic tag is hybridized to the target DNA. In preparing the devices according to the protocols illustrated in FIGS. 1(a) and 1(b), the binding kinetics of the interaction between the capture binding member (e.g., capture antibody or capture DNA) and the target member (e.g., analyte or target DNA) may be of interest. In such embodiments, the target and labeled member are contacted with each other first under binding conditions, and the resultant complex contacted with the sensor surface. Alternatively, in preparing the devices according to the protocols illustrated in FIGS. 1(a) and 1(b), the binding kinetics of the interaction between the labeled binding member (e.g., labeled antibody or labeled DNA) and the target member (e.g., analyte or target DNA) may be of interest. In such embodiments, the target and capture member will be contacted with each other first under binding conditions, and the resultant sensor surface associated complex contacted with labeled member.

The contacting (including applying) steps described above are carried out under conditions in which the binding interaction of interest may occur. While the temperature of contact may vary, in some instances the temperature ranges from 1 to 95° C., such as 5 to 60° C. and including 20 to 40° C. The various components of the assay may be present in an aqueous medium, which may or may not include a number of additional components, e.g., salts, buffering agents, etc. In some instances, contact is carried out under stringent conditions. Stringent conditions may be characterized by temperatures ranging from 15 to 35° C., such as 20 to 30° C. less than the melting temperature of the probe target duplexes, which melting temperature is dependent on a number of parameters, e.g., temperature, buffer compositions, size of probes and targets, concentration of probes and targets, etc. As such, the temperature of hybridization may range from about 55 to 70° C., usually from about 60 to 68° C. In the presence of denaturing agents, the temperature may range from about 35 to 45, usually from about 37 to 42° C. The stringent hybridization conditions may be characterized by the presence of a hybridization buffer, where the buffer is characterized by one or more of the following characteristics: (a) having a high salt concentration, e.g. 3 to 6×SSC (or other salts with similar concentrations); (b) the presence of detergents, such as SDS (from 0.1 to 20%), triton X100 (from 0.01 to 1%), monidet NP40 (from 0.1 to 5%) etc.; (c) other additives, like EDTA (e.g., from 0.1 to 1 µM), tetramethylammonium chloride; (d) accelerating agents, e.g. PEG, dextran sulfate (from 5 to 10%), CTAB, SDS and the like; (e) denaturing agents, e.g. formamide, urea, etc.; and the like. Stringent conditions are conditions in which the stringency is at least as great as the specific conditions described above.

The sample that is contacted with the sensor surface may be a simple sample or complex sample. By "simple sample" is meant a sample that includes one or more members of the binding interaction and few, if any, other molecular species apart from the solvent. By "complex sample" is meant a sample that includes the one or more members of the binding interaction of interest and also includes many different proteins and other molecules that are not of interest. In certain embodiments, the complex sample is a blood sample, by which is blood or a fraction thereof, e.g., serum. In certain embodiments, the complex sample is a serum sample. In certain embodiments, the complex sample assayed in the methods of the invention is one that includes 10 or more, such as 20 or more, including 100 or more, e.g., $10^3$ or more, $10^4$ or more (such as 15,000; 20,000 or even 25,000 or more) distinct (i.e., different) molecular entities that differ from each other in terms of molecular structure.

Obtaining a Real-Time Signal from a Magnetic Sensor

Following production of the device that includes the magnetic sensor in contact with an assay mixture (including the binding members of the binding interaction of interest and a magnetic label, e.g., as described above), aspects of the methods include obtaining a real-time signal from the magnetic sensor. As such, certain embodiments include obtaining a real-time signal from the device. Accordingly, the evolution in real time of the signal associated with the occurrence of the binding interaction of interest may be observed. The real-time signal is made up of two or more data points obtained over a given period of time of interest, where in certain embodiments the signal obtained is a continuous set of data points (e.g., in the form of a trace) obtained continuously over a given period of time of interest. The time period of interest may vary, ranging in some instances from 1 second to 10 hours, such as 10 seconds to 1 hour and including 1 minute to 15 minutes. The number of data points in the signal may also vary, where in some instances, the number of data points is sufficient to provide a continuous stretch of data over the time course of the real-time signal.

In some embodiments, the signal is observed while the assay system is in the "wet" condition, that is, with a solution containing assay components (e.g., the binding members and magnetic label) still in contact with the sensor surface. As such, there is no need to wash away all of the non-binding or irrelevant molecules. This "wet" detection is possible because the magnetic field generated by the magnetic tag nanoparticle (e.g., with a diameter of 150 nm or less as described elsewhere) decreases rapidly as the distance from the nanoparticle increases. Therefore, the magnetic field at the sensor of the label bound to the captured binding members exceeds the magnetic field from the unbound magnetic labels in the solution, which are both at a greater distance from the detector and are in Brownian motion. The term "proximity detection" as used herein refers to this dominance at the sensor of the bound nanoparticles. Under the "proximity detection" scheme specifically bound magnetically labeled conjugates at the sensor surface can be quantified without washing off the nonspecific magnetic nanotags in the solution.

For a given binding interaction of interest, an assay may include obtaining a real-time signal for a single binding pair member concentration or multiple binding pair concentrations, such as 2 or more, 3 or more, 5 or more, 10 or more, 100 or more, or even 1,000 or more different concentrations. A given assay may contact the same sensor having the same capture probe concentration with multiple different binding pair member concentrations, or vice versa or a combination of different concentrations of capture probes and binding pair members, as desired.

Quantitatively Determining a Binding Kinetic Parameter from the Real-Time Signal As summarized above, following obtainment of the real-time signal, the methods may include quantitatively determining a binding kinetic parameter of a molecular binding interaction from the real-time signal. In other words, the real-time signal is employed to quantitatively determine the binding kinetic parameters of interest, such that the binding kinetic parameters of interest are obtained from the real-time signal.

In some instances, the binding kinetic parameters of interest are quantitatively determined by processing the real-time signal with a fitting algorithm. By fitting algorithm is meant a set of rules that determines the binding kinetic parameters of interest by fitting equations to the real-time signal or signals obtained from a given assay, e.g., as described above. Any convenient fitting algorithm may be employed.

Figure 2:
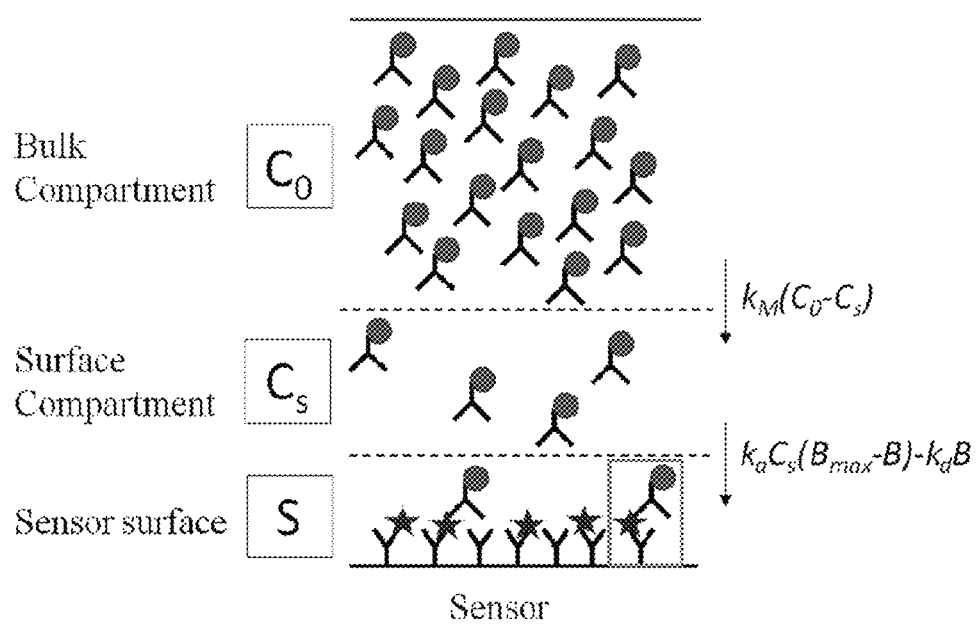
FIG. 2 provides a schematic of the two-compartment reaction-diffusion model, according to embodiments of the present disclosure. Labeled antibodies move to the sensor surface via transport process and then bind and release via conjugation flux.
Figure 3A:
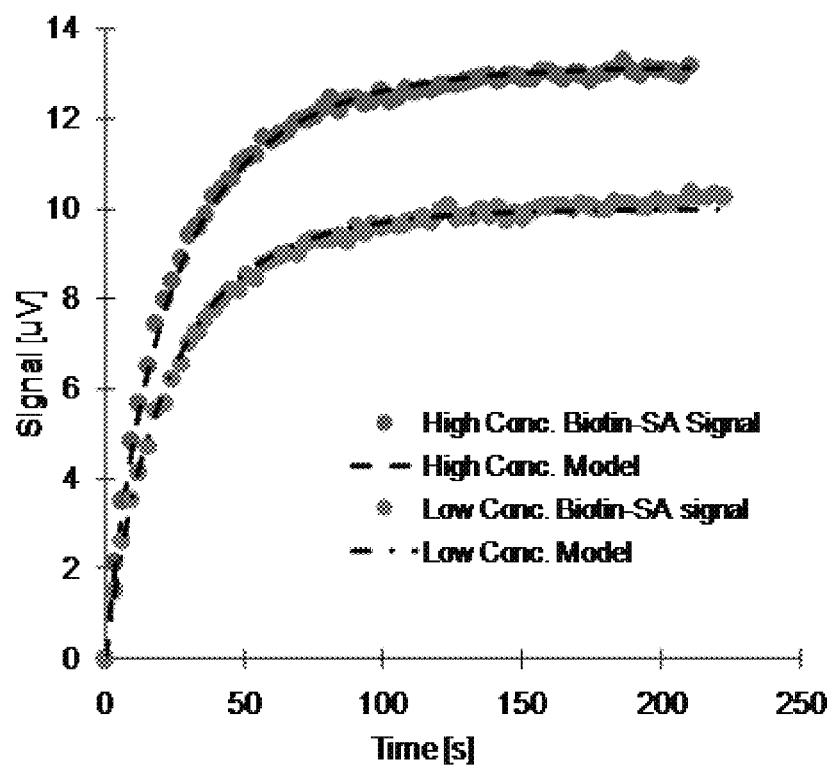
FIG. 3 shows graphs of a comparison of a kinetic model to real-time binding data for streptavidin-biotin binding interactions (a) and EpCAM antibody to EpCAM antigen (b), according to embodiments of the present disclosure. Once the model was fit to the binding data, the association rate constant, dissociation rate constant, and diffusion-limited rate constant were calculated from the fitting. The real-time binding curves shown in FIGS. 3(c) and 3(d) show monitoring of binding kinetics of CEA antibody to CEA antigen in parallel experiments in order to compare magnetonanosensor and surface plasmon resonance (SPR) systems respectively, according to embodiments of the present disclosure. The GMR biosensor had a calculated value for $k_a$ of $5.0 \times 10^4$ $M^{-1}$ $s^{-1}$ and $k_d$ of $4.4 \times 10^{-4}$ $s^{-1}$ while SPR experiments yielded a $k_a$ of $4.44 \times 10^4$ $M^{-1}$ $s^{-1}$ and $k_d$ of $1.17 \times 10^{-4}$ $s^{-1}$.
Figure 3B:
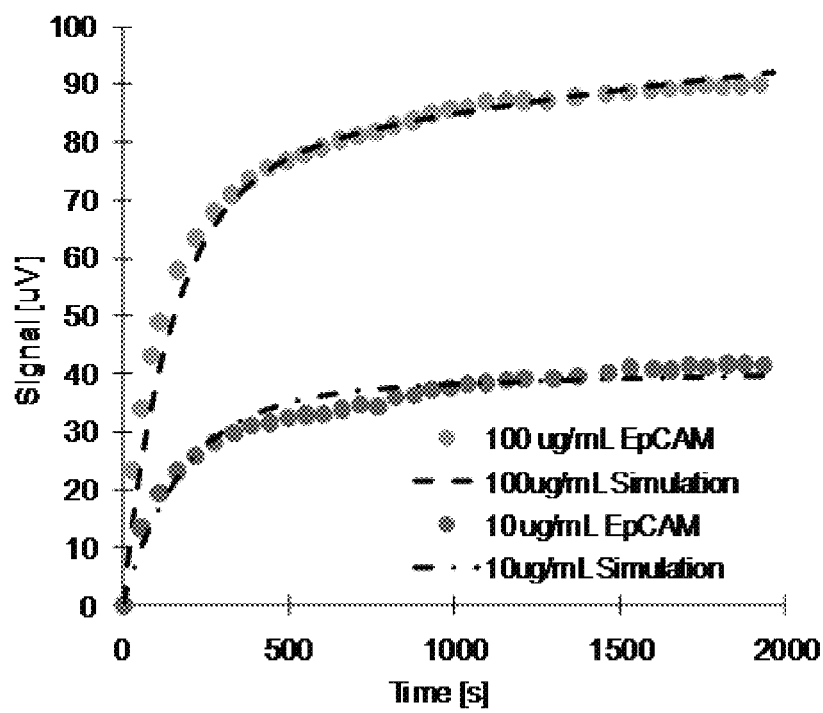
Figure 3C:
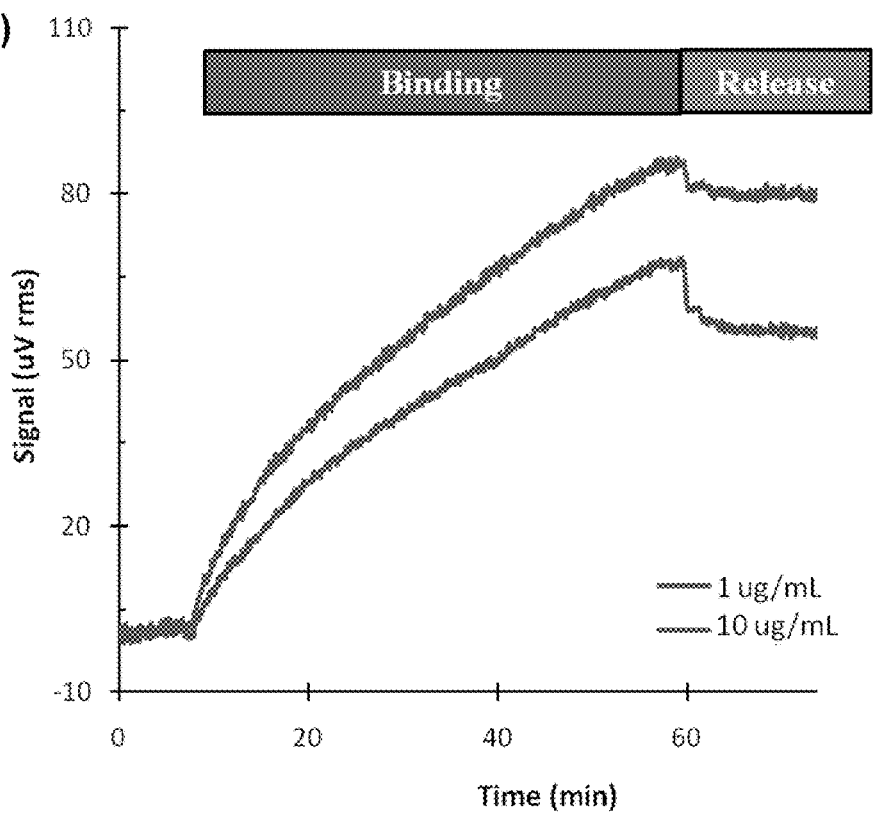
Figure 3D:
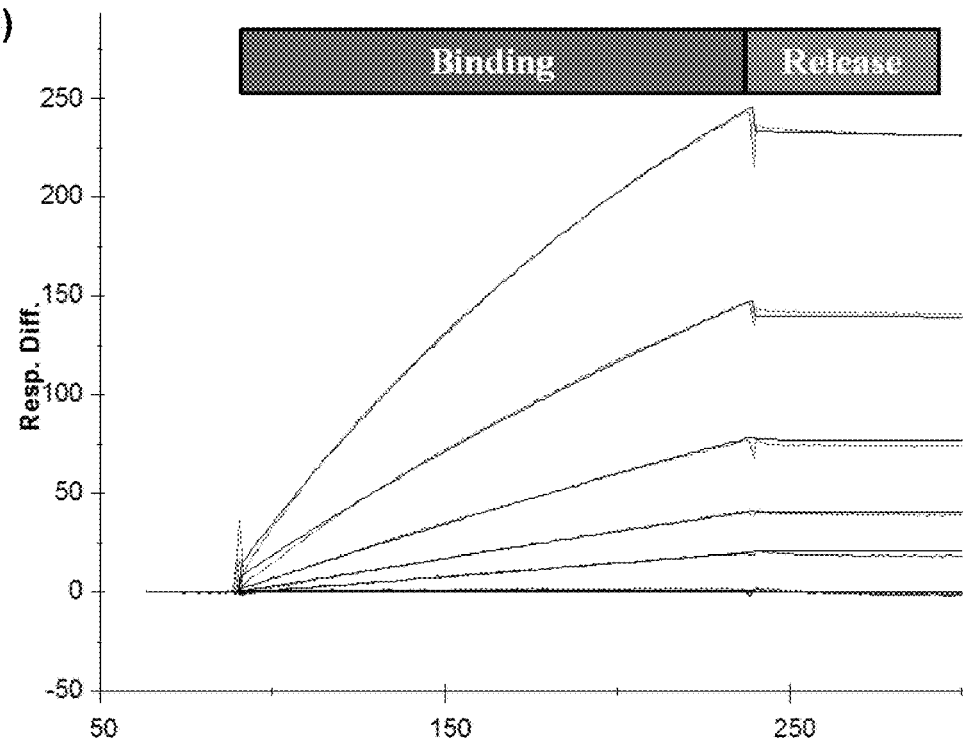

In some embodiments, a two-compartment model is used to fit the real-time data. A two-compartment model of interest assumes that the magnetically labeled binding molecule in solution approaches the surface bound binding partner, e.g., captured first biomolecule, via transport process (diffusion and flow) and then binds to the surface bound binding partner via the chemical processes of association and dissociation. In these instances, the two compartments in the model are the bulk compartment and the surface compartment. FIG. 2 provides a schematic of the two-compartment reaction-diffusion model employed in some embodiments, where labeled molecules (illustrated as labeled antibodies) move to the sensor surface via transport process and then bind and release via conjugation flux. In some instances, the concentration of the magnetically labeled molecule is assumed to be uniform in each compartment and only the magnetically labeled molecules in the surface compartment ($C_s$) will react with the binding sites on the sensor surface and the labeled molecules in the bulk compartment ($C_0$) will diffuse to the surface. In some instances, the employed two-compartment model does not assume that "rapid mixing" is taking place.

The governing equations for this system are written as:

$$\frac{dC_s}{dt} k_M (C_0 - C_s) - k_a C_s (B_{max} - B) + k_d B \quad (1)$$

$$\frac{dB}{dt} = k_a C_s (B_{max} - B) - k_d B \quad (2)$$

with boundary conditions being:

$$C_s|_{t=0} = C_0 \quad (3)$$

$$B|_{t=0} = 0 \quad (4)$$

where B is the concentration of bound first/second biomolecule conjugate on the sensor surface, $B_{max}$ is the available receptor concentration at beginning, $k_a$ ($=k_{on}$) is the association rate constant, $k_d$ ($=k_{off}$) is the dissociation rate constant, and $k_M$ is the diffusion-limited rate constant. As there is no analytical solution to this general differential equation set, a numerical fitting algorithm is employed.

The first equation provided above is employed to describe the concentration of labeled second molecule in the surface compartment, $C_s$. This equation assumes that the inflow of labeled second molecule to the surface compartment through diffusion from the bulk compartment minus the net outflow of second molecule through association and dissociation with the receptors equals to the rate of increase of $C_s$. Diffusion is the only mass transport mechanism in those embodiments where the whole system is left still during the binding process.

The second equation is used to describe the concentration of sensor surface bound first/second biomolecule conjugates, B. This equation assumes that the inflow of labeled second biomolecule through association minus the dissociation equals to the rate of increase of B.

Finally, the real-time signal is assumed to proportional to B, i.e., $$V = gB, \quad V_{max} = gB_{max}. \tag{5}$$

There are five unknown parameters that will be the fitting parameters, $k_a$, $k_d$, $k_M$, g, and $V_{max}$. Among these five fitting parameters, $k_a$, $k_d$, $k_M$, and g are assumed to be the same for all sensors that have the same capture, first and second biomolecules in one assay and therefore are referred to as global fitting parameters; $V_{max}$ is different for each sensor because it is difficult to control exactly the concentration of surface bound binding partners, e.g., capture molecules, first biomolecules, immobilized on the sensor surface. Even in one assay when all sensors are on the same chip and are treated the same, there will be some variations in $B_{max}$ and therefore some variations in $V_{max}$.

In some instances, the two-compartment model is a modification of the two-compartment model described in D. Myszka, et al., *Anal. Biochem.* (1998) 265:326-330, e.g., where the model has been modified to comport with the parameters described above.

Where desired, the concentrations of immobilized binding partners may be intentionally varied across sensors so signal curves with different shapes can be acquired and analyzed, e.g., in a protocol referred to as global analysis or global fitting. In such instances, the two compartment binding model (e.g., as described above) is fitted simultaneously to multiple real-time signals obtained with different analyte concentrations C (and/or with different levels of surface derivatization $B_{max}$). Known in the art as "global fitting" and based on the real-time data, such global fitting establishes whether a single global $k_a$ or $k_d$ will provide a good fit to all the data. The results of the completed fit may be presented to an operator graphically, displaying the fitted curves overlaid on the original real-time data curves.

Where desired, the closeness of the fit may also be presented by the chi-squared ($X^2$) value, a standard statistical measure. In some instances, when the chi-squared value is in the same magnitude as the noise in experiments, good fitting is considered to be present. The coefficient of determination, which may be referred to as $R^2$, may also be employed as an indicator of the goodness of fitting. $R^2$ may be defined as following: if the signal curve is $s_i$ and the fitting curve is $f_i$, i=1, 2, ... n when there are n points in a signal curve, then $$R^2 = 1 - \frac{SS_{err}}{SS_{tot}} \tag{6}$$

where $$SS_{err} = \sum_i (f_i - s_i)^2$$

is the sum of square errors of the fitting, and $$SS_{tot} = \sum_i (s_i - \bar{s})^2$$

is the total variations of the signal

If there are N signal curves from one assay, each signal curve will have a $R^2$ value, the average value of $1-R^2$ will be minimized to get the best fit to all N curves.

In some instances, "residual plots" may also be provided which give a graphical indication of how the experimental data deviate from the fitted curve showing the difference between the experimental and fitted data for each curve. The operator may then decide if the fit is good enough. If not, the real time signal or signals exhibiting the poorest fit may be excluded and the fitting procedure rerun with the reduced set of real time signals. This procedure may be repeated until the fit is satisfactory.

Another fitting algorithm of interest includes the specific fitting algorithm disclosed in the Experimental section, infra.

Where desired, the above quantitative determination protocol may be carried out with the aid of software and/or hardware configured to perform the above described protocol.

Multiplex Analysis

Aspects of the invention include the multiplex analysis of two or more distinct binding interactions with the same sensor. By "multiplex analysis" is meant that two or more distinct binding interactions between different sets of binding molecules, in which the binding molecules and/or the magnetically labeled molecules are different from each other, e.g., by different sequence, are quantitatively analyzed. In some instances the number of sets is 2 or more, such as 4 or more, 6 or more, 8 or more, etc., up to 20 or more, e.g., 50 or more, including 100 or more, or 1000 or more, distinct sets. As such, in some cases, the magnetic sensor device may comprise two or more distinct magnetic sensors that each specifically detects a distinct binding interaction, such as 2 or more, or 4 or more, 6 or more, 8 or more, etc., up to 20 or more, e.g., 50 or more, including 100 or more, or 1000 or more, distinct magnetic sensors. In certain embodiments, of interest is the multiplex analysis of 2 to 1000 distinct binding interactions, such as 2 to 50, or 2 to 20 distinct binding interactions. Thus, in these embodiments, the magnetic sensor device may include 2 to 1000 distinct magnetic sensors that each specifically analyzes a distinct binding interaction, such as 4 to 1000 distinct magnetic sensors. In other cases, the magnetic sensor device may include 20 or less distinct magnetic sensors that each specifically analyzes a distinct binding interaction, such as 10 or less, including 4 or less distinct magnetic sensors.

Devices and Systems

Aspects of the invention further include magnetic sensor devices and systems that are configured to quantitatively determine one or more binding kinetic parameters of a molecular binding interaction of interest. The devices and systems generally include a magnetic sensor; and a quantitative analysis module (e.g., processor) configured to receive a real-time signal from the magnetic sensor and quantitatively determine a binding kinetic parameter of a molecular binding interaction from the real-time signal. These two components may be integrated into the same article of manufacture as a single device, or distributed among two or more different devices (e.g., as a system) where the two or more different devices are in communication with each other, e.g., via a wired or wireless communication protocol.

Accordingly, aspects of the invention further include systems, e.g., computer based systems, which are configured to quantitatively assess binding interactions as described above. A "computer-based system" refers to the hardware means, software means, and data storage means used to analyze the information of the present invention. The minimum hardware of embodiments of the computer-based systems includes a central processing unit (CPU) (e.g., a processor), input means, output means, and data storage, means. Any one of the currently available computer-based system may be suitable for use in the embodiments disclosed herein. The data storage means may include any manufacture including a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of an electronic controller, mainframe, server or personal computer (e.g., desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Embodiments of the subject systems may include the following components: (a) a communications module for facilitating information transfer between the system and one or more users, e.g., via a user computer or workstation; and (b) a processing module for performing one or more tasks involved in the disclosed quantitative analysis methods.

In certain embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein may be accomplished using any convenient method and techniques.

In addition to the sensor device and quantitative analysis module, systems and devices of the invention may include a number of additional components, such as data output devices, e.g., monitors, printers, and/or speakers, data input devices, e.g., interface ports, keyboards, etc., fluid handling components, power sources, etc.

Utility

The subject methods, systems and kits find use in a variety of different applications where quantitative determination of a binding kinetic parameter of a binding interaction of interest is desired. In certain embodiments, the binding interaction is a binding interaction, such as, but not limited to, nucleic acid hybridization, a protein-protein interaction (e.g., as described in greater detail in the Experimental Section, below), a receptor-ligand interaction, an enzyme-substrate interaction, a protein-nucleic acid interaction, and the like.

In some instances, the subject methods, systems and kits find use in drug development protocols where the observation in real-time of molecular binding interactions may be desired. For example, drug development protocols may use the subject methods, systems and kits to monitor molecular the binding interactions between antibodies and antigens, or hybridization interactions between nucleic acids, or binding interactions between proteins, or binding interactions between receptors and ligands, or binding interactions between enzymes and substrates, or binding interactions between proteins and nucleic acids, and the like, in real time. For instance, CEA and VEGF are tumor markers and anti-VEGF antibody drugs, such as bevacizumab (Avastin; Genentech/Roche), are effective anti-cancer drugs. Another example is anti-EpCAM antibody, which has been formulated into a chemotherapeutic drug, edrecolomab. Monitoring binding interactions such as these may facilitate the development of other antibody-based drugs.

The subject methods, systems and kits also find use in analyzing molecular binding interactions between binding pairs that are included in complex samples. In some instances, the complex samples may be analyzed directly without separating the binding molecules of interest from the other proteins or molecules that are not of interest that may be in the sample. In certain cases, non-specific binding of proteins or molecules that are not of interest and unbound magnetic nanoparticles produce substantially no detectable signal in the subject methods, systems and kits. Thus, the subject methods, systems and kits find use in assay protocols where complex samples may be used and where the binding interactions of interest may be monitored in real-time with no washing of the sensor necessary for detection of the binding interactions of interest.

The real time binding assay and kinetic model disclosed herein may find use in applications such as epitope mapping. For example, the GMR sensor array has the ability to perform epitope mapping in a highly parallel fashion. Using capture antibodies, antigen can be selectively immobilized in a specific intra-molecular configuration on the sensor surface. The kinetic interaction of exposed epitopes on the captured antigen can be probed for affinity to various receptors or antibodies. For example, epidermal growth factor receptor (EGFR) is capable of binding EGF itself as well as proteins containing EGF-like repeats, such as EpCAM. By capturing proteins with EGF-like repeats using different monoclonal antibodies, and examining the binding of EGFR to these oriented proteins, an epitope map can be determined to evaluate the affinity of EGFR for various ligands containing EGF-like repeats. Using GMR sensors to probe exposed epitopes has applications ranging from massive screens of drug interactions with specific targets to parallel screening for specific domains of interest in the proteome.

The subject methods, systems and kits also find use in monitoring molecular binding interactions in both space and time. For example, the subject methods, systems and kits may be used to monitor localized cell-cell communication via cellular protein secretome analysis. By monitoring the diffusion of cellular protein secretions in space and time, the mechanisms of cell-cell communication may be determined.

The subject methods, systems and kits also find use in basic science research for understanding receptor-ligand binding interactions involved in signal transduction in cell biology or for profiling specific compounds of interest against an entire proteome. In addition, applications to clinical medicine are vast ranging from massive screens in directed protein evolution studies to investigating drug on-target and off-target cross-reaction binding kinetics.

Computer Related Embodiments

Aspects of certain embodiments further include a variety of computer-related embodiments. Specifically, the data analysis methods described in the previous sections may be performed using a computer. Accordingly, embodiments provide a computer-based system for analyzing data produced using the above methods in order to provide quantitative determination of a binding kinetic parameter of a binding interaction of interest.

In certain embodiments, the methods are coded onto a computer-readable medium in the form of "programming", where the term "computer readable medium" as used herein refers to any storage or transmission medium that participates in providing instructions and/or data to a computer for execution and/or processing. Examples of storage media include floppy disks, magnetic tape, CD-ROM, DVD, Blu-Ray, a hard disk drive, a ROM or integrated circuit, a magneto-optical disk, or a computer readable card such as a PCMCIA card or flash memory card, and the like, whether or not such devices are internal or external to the computer. A file containing information may be "stored" on computer readable medium, where "storing" means recording information such that it is accessible and retrievable at a later date by a computer. Of interest as media are non-transitory media, i.e., physical media in which the programming is associated with, such as recorded onto, a physical structure. Non-transitory media does not include electronic signals transmitted via a wireless protocol.

With respect to computer readable media, "permanent memory" refers to memory that is permanent. Permanent memory is not erased by termination of the electrical supply to a computer or processor. Computer hard-drive, CD-ROM, Blu-Ray, floppy disk and DVD are all examples of permanent memory. Random Access Memory (RAM) is an example of non-permanent memory. A file in permanent memory may be editable and re-writable.

Kits

Also provided are kits for practicing one or more embodiments of the above-described methods. The subject kits may vary, and may include various devices and reagents. Reagents and devices of interest include those mentioned herein with respect to magnetic sensor devices or components thereof (such as a magnetic sensor array or chip), magnetic nanoparticles, binding agents, buffers, etc.

In some instances, the kits include at least reagents finding use in the methods (e.g., as described above); and a computer readable medium having a computer program stored thereon, wherein the computer program, when loaded into a computer, operates the computer to quantitatively determine a binding kinetic parameter of a binding interaction between the first and second molecules from a real-time signal obtained from a magnetic sensor; and a physical substrate having an address from which to obtain the computer program.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, Blu-Ray, etc., on which the information has been recorded. Yet another means that may be present is a website address which may be used via the Internet to access the information at a removed site. Any convenient means may be present in the kits.

The following examples are offered by way of illustration and not by way of limitation.

EXPERIMENTAL

I. Determination of Binding Kinetics

A. Materials & Methods

A giant magnetoresistance (GMR) sensor array as described in Osterfield et al., *Proc. Nat'l Acad. Sci USA* (2008) 150:20637-206340 and Xu et al., *Biosens. Bioelectron* (2008) 24:99-103 was employed in the following general protocol:

1. Surface Functionalization: Sensor surfaces were functionalized to provide for stable association of a binding pair member, e.g., a capture antibody, first biomolecule, etc., onto the sensor surface. A cationic polymer such as polyethyleneimine (PEI) can be used to nonspecifically bind charged antibodies to the sensor surface via physisorption. Alternatively, a covalent chemistry can be used utilizing free amines on the antibody or free thiol groups. Additional details regarding surface functionalization for stable attachment of oligonucleotides is provided in Xu et al., *Biosens. Bioelectron* (2008) 24:99-103 and for antibodies is provided in Osterfield et al., *Proc. Nat'l Acad. Sci USA* (2008) 150:20637-206340. The binding pair member of interest was then contacted with the sensor surface to stably associate the binding member to the sensor surface.

2. Following surface functionalization and binding pair association, the sensor surface was blocked to prevent non-specific binding during the assay. In order to block the surface, a blocking buffer comprised of 1% BSA in PBS was added to the reaction well for one hour. Additional blocking protocols that may find use are described in Xu et al., *Biosens. Bioelectron* (2008) 24:99-103 and Osterfield et al., *Proc. Nat'l Acad. Sci USA* (2008) 150:20637-206340.

3. Following blocking, the sensor surface was contacted with a solution of the first biomolecule of interest, e.g., a purified solution of the first biomolecule or a complex sample that included the first biomolecule. For this step, a reaction well containing a solution of ~1 nL-100 μL was used and the incubation time ranged from 5 minutes to 2 hours depending on the application.

4. Following incubation, a solution containing the second biomolecule pre-labeled with the tag of interest (e.g., magnetic nanoparticle particle) was contacted with the sensor surface.
5. Next, the binding kinetics of the second biomolecule to the first biomolecule were monitored and used to calculate binding rate constants based on the binding trajectory.

B. Results & Discussion

Real-time data from GMR biosensors were used to calculate on and off rates of biotin-streptavidin interactions (FIG. 3($a$)). Biotinylated double stranded DNA was immobilized on the sensor surface and streptavidin labeled magnetic tags were added to the system. An on-rate of $4.45 \times 10^6$ $M^{-1} s^{-1}$ was calculated with a fitting error of 3.2% and a $k_M$ of $4.4 \times 10^{-4} s^{-1}$. The same biotin-streptavidin binding experiment was performed when using the BIAcore 3000 surface plasmon resonance (SPR) instrument and measured an on-rate of $5.5 \times 10^6$ $M^{-1} s^{-1}$, in close agreement with the GMR sensor array.

Next, the ability to use arrays of GMR sensors to investigate antibody-antigen binding kinetics (FIG. 2) was demonstrated. Sensors in the array were functionalized with EpCAM protein on five to ten replica sensors at 100 µg/mL and 10 µg/mL. Using the model, it was possible to simulate the binding process of magnetically labeled antibodies to immobilized antigens present at several concentrations. From the fitted data (FIG. 3($b$)), it was determined that for the chosen EpCAM antibody-antigen interaction, $k_a$ was $2.93 \times 10^5$ $M^{-1} s^{-1}$, $k_d$ was $2.83 \times 10^{-3}$ $s^{-1}$ with a total fitting error of 3.4% and a $k_M$ of $4.2 \times 10^{-4} s^{-1}$.

Similar real-time experiments were run in order to quantify high affinity CEA antigen-antibody binding kinetics. 1 µg/mL and 10 µg/mL of CEA were immobilized on the GMR sensor surface and 20 µg/mL, 10 µg/mL, 5 µg/mL, 2.5 µg/mL and 1.2 µg/mL were tested via SPR analysis. Association and dissociation rate constants were monitored on each platform and results compared (FIGS. 3($c$) and 3($d$)). Again, GMR sensor array and SPR yielded kinetic rate constants that were similar. For the GMR biosensor, $k_a$ was determined to be $5.0 \times 10^4$ $M^{-1} s^{-1}$ and $k_d$ was $4.4 \times 10^{-4} s^{-1}$ while SPR experiments yielded a $k_a$ of $4.44 \times 10^4$ $M^{-1} s^{-1}$ and $k_d$ of $1.17 \times 10^{-4} s^{-1}$. Therefore, these results demonstrated that magnetically responsive biosensors can be used to accurately measure binding rate constants.

II. High-Throughput Analysis and Kinetic Model of Protein Interactions for Antibody Development and Drug Screening A. Materials and Methods 1. Sensor The giant magnetoresistive (GMR) sensor used in the experiment had a bottom spin valve structure of the type: Si/Ta(5)/seed layer/IrMn(8)/CoFe(2)/Ru/(0.8)/CoFe(2)/Cu (2.3)/CoFe(1.5)/Ta(3), all numbers in parenthesis are in nanometers. Each chip contained an array of GMR sensors, which were connected to peripheral bonding pads by a 300 nm thick Ta/Au/Ta lead. To protect the sensors and leads from corrosion, two passivation layers were deposited by ion beam sputtering: first, a thin passivation layer of $SiO_2$(10 nm)/$Si_3N_4$(20 nm)/$SiO_2$(10 nm) was deposited above all sensors and leads, exposing only the bonding pad area; second a thick passivation layer of $SiO_2$(100 nm)/$Si_3N_4$(150 nm)/$SiO_2$(100 nm) was deposited on top of the reference sensors and leads, exposing the active sensors and bonding pad area. The magnetoresistive ratio was approximately 12% after patterning. The pinning direction of the spin valve was in-plane and perpendicular to the sensor strip. The easy axis of the free layer was set by the shape anisotropy to be parallel with the sensor strip. This configuration allowed the GMR sensors to work at the most sensitive region of their MR transfer curves.

Due to the GMR effect, the resistance of the sensor changed with the orientation of the magnetization of the two magnetic layers, which were separated by a copper spacer layer:

$$R(\theta) = R_0 - \frac{1}{2}\delta R_{max} \cos\theta \quad (\text{M.1})$$

Here, $R_0$ is the resistance under zero magnetic field, $\delta R_{max}$ is the maximum resistance change and $\theta$ is the angle between the magnetization of the two magnetic layers. In the bottom spin valve structure, the magnetization of bottom magnetic layer (pinned layer) was pinned to a fixed direction, while the magnetic orientation of the top magnetic layer (free layer) was able to freely rotate with the external magnetic field. As a result, the stray field from the magnetic label can change the magnetization of the free layer and therefore change the resistance of the sensor.

2. Magnetic Label

The magnetic labels were obtained from Miltenyi Biotech Inc., referred to as "MACS" particles. Each MACS particle was a cluster of 10 nm $Fe_2O_3$ nanoparticles held together by a matrix of dextran. Due to the small size of the $Fe_2O_3$ nanoparticles, the MACS particle was superparamagnetic, with an overall diameter of 50 nm and contained 10% magnetic material (wt/wt). MACS particles were functionalized with the corresponding analyte being studied, e.g., for EpCAM (CEA, VEGF) experiments, the MACS particles were functionalized with EpCam (CEA, VEGF) antibodies; for biotin-streptavidin experiments, the MACS particles were functionalized with streptavidin.

3. Surface Chemistry

The sensor surface was first rinsed with acetone, methanol and isopropanol. Subsequently, the sensors were exposed to oxygen plasma for three minutes. A 2% (w/v) polyallylamine solution in deionized water was applied to the sensor for 5 minutes. Other solutions may be used as desired, such as, but not limited to, solutions including anhydrise, poly allyl carboxylates, and the like. The chips were then rinsed with deionized water and baked at 150° C. for 45 minutes. For carboxylated surfaces, a 10% (w/v) solution of EDC and 10% (w/v) solution of NHS was then added to the sensor surface at room temperature for 1 hour. Capture protein (EpCAM (960-EP-050 from RD Systems), CEA (4128-CM-050 from RD Systems) or VEGF (293-VE165 from RD Systems)) or capture antibody (antibody to EpCAM (ab20160 from Abcam or 960 from R&D), CEA (5910 from BiosPacific) or VEGF (ab69479 from Abcam)) was robotically deposited over each sensor in 360 picoliter droplets 3 times (total volume of 1 nanoliter). In order to monitor reproducibility, 3 to 8 sensors, randomly distributed across the GMR sensor array, were incubated with the same capture protein. The control sensors were immobilized in a similar fashion with either BSA at 1 mg/mL or a non-complementary antibody (typically anti survivin antibody (H00000332-P01 from Novus Biologicals, LLC) at 500 µg/mL. The entire surface of the sensor array was blocked with 1 mg/mL of BSA in PBS for 30 minutes.

4. Kinetic Assay

Alternatively, the kinetic assay can be modeled as follows:

After the sensor surface was functionalized with the appropriate capture protein, the GMR sensor array was placed in the test station and monitored in real time. The BSA blocking buffer was washed away and a 50 µL solution of the magnetically labeled detection antibody (made as described above) was added to the reaction well. The GMR sensor array was monitored over time as the magnetically labeled detection antibody bound to the corresponding protein. The binding curves, unique to each protein, could then be plotted and the binding rate constants could be determined. The assay was run for 5 minutes.

5. Model and Fitting

The process of two molecules interacting to produce one product can be generalized as:

$$C_s + L \leftrightarrow n$$

Where $C_S$ is the concentration of reactant in solution near the surface, L is the concentration of the ligand or receptor on the surface, and n is the surface concentration of the product of the interaction. In simple models, at least one of the reactants is assumed to be in excess. However, in the model presented herein, the reactant receptors on the sensor surface are not replenished. As a result, the sum of L and n should be equal to the original concentration of L.

$$[L] + [n] = [L]_0 = [n_{max}\text{ }]$$ 

For the model $[L]_0 = [n_{max}]$, where $n_{max}$ is limited by the maximum concentration of close packed MNPs, not by the maximum concentration of analyte on the surface. The number of magnetically labeled antibodies bound to their targets, n(t), at a given time was monitored using GMR biosensor arrays. In order to quantify the binding rate constants of this interaction, an analytical model was derived by assuming the mass conservation of reactants within a volume V and reactive sensor surface of A. Equation M1.1, below, expresses the rate of change of labeled antibody in the solution, while equation M1.2 expresses the rate of binding of the labeled antibody to the sensor surface:

$$V\frac{dC_S}{dt} = -Ak_{on}C_S(n_{max} - n) + Ak_{off}n \quad (M1.1)$$

$$A\frac{dn}{dt} = Ak_{on}C_S(n_{max} - n) - Ak_{off}n \quad (M1.2)$$

where $C_s$ is the concentration of the magnetically tagged antibody at the surface of the sensor, $C_0$ is the bulk concentration of magnetically tagged antibody, $n_{max}$ is the maximum moles of potential binding sites per area on the sensor surface and n is the surface concentration of bound MNP-antibody-antigen complexes that have formed over the sensor. V is the volume of the solution above the sensor and A is the reaction area (in this case the surface area of each sensor). In addition, $k_{on}$ is the association rate constant and $k_{off}$ is the dissociation rate constant.

This system of equations can be simplified by assuming that $k_{off}$ is zero since the antibody-antigen dissociation is negligible on the time scale of the present experiments. Therefore, by summing the simplified equations M1.1 and M1.2, the conservation expression is as follows:

$$V\frac{dC_S}{dt} + A\frac{dn}{dt} = 0 \quad (M1.3)$$

Given the boundary conditions at t=0, n=0 and $C_s = C_0$, gives $C_s = C_0 - nA/V$, so $$\frac{dn}{dt} = k_{on}\left(C_0 - n * \frac{A}{V}\right)(n_{max} - n) \quad (M1.4)$$

The terms within parentheses represent the depletion of bulk reactants and of available surface sites, respectively. This equation has the analytical solution in Eq. M1.5, which accurately models the observed binding kinetics.

$$n = C_0 \frac{V}{A}\left[\frac{1 - e^{-k_{on}(A/V)(C_0(V/A) - n_{max})t}}{\frac{C_0 V}{n_{max}A} - e^{-k_{on}(A/V)(C_0(V/A) - n_{max})t}}\right] \quad (M1.5)$$

$C_s$ is the concentration of the magnetically tagged antibody at the surface of the sensor, $C_0$ is the bulk concentration of magnetically tagged antibody, $n_{max}$ is the maximum moles of surface binding sites per area, and n is the surface concentration of bound MNP-antibody-antigen complexes that have formed over the sensor. V is the volume of the solution above the sensor and A is the reaction area (in this case the surface area of each sensor). In the solution, there is a ratio of V/A, which can be thought of as the characteristic diffusion height. Anything in solution above this characteristic height will not bind to the sensor within the timeframe of the experiment. In addition, $k_{on}$ is the association rate constant and $k_{off}$ is the dissociation rate constant.

Since both kinetics in a volume and at a surface are discussed, the different dimensions; n and $n_{max}$ are expressed in moles/cm$^2$ whereas $C_s$ and $C_o$ are expressed in moles/cm$^3$. By multiplying the solution rates by a volume and the surface rates by an area, the binding rate constants can be represented in each equation in the same units (moles per time).

There are four fitting parameters $k_{on}$, $C_0$, $n_{max}$ and V/A (which is the effective thickness of the reactive part of the solution). Among them, $k_{on}$ and V/A are "global fitting parameters", which are the same for all signal curves from the same receptor-analyte pair; while $n_{max}$ and $C_0$ are "local fitting parameter", which will be different for different signal curves because the surface concentration of analyte or the solution concentration of antibody-MNP complexes may not be uniform across all experiments.

When $C_0 V/A \gg n_{max}$, the analytical model reduces to the Langmuir model.

$$n = C_0 \frac{V}{A}\left[\frac{1 - e^{-k_{on}(A/V)(C_0(V/A) - n_{max})^0 t}}{\frac{C_0 V}{n_{max}A} - e^{-k_{on}(A/V)C_0(V/A) - n_{max})^0 t}}\right] \quad (M1.6)$$

$$n = \cancel{C_0} \frac{\cancel{V}}{\cancel{A}}\left[\frac{1 - e^{-k_{on}(A/V)(C_0(V/A))t}}{\frac{\cancel{C_0 V}}{n_{max}\cancel{A}}}\right]$$

$$n = n_{max}(1 - e^{-k_{on}C_0 t})$$

This equation matches the solution to the Langmuir binding model when assuming $k_{off}$ is negligible on the time scale of the experiment. The above equation is identical to Equation M.25 derived below.

6. Fitting Error

Fitting error is defined as the following: if N signal curves are measured from one chip, and curve j has $n_j$ data points, and if $D_{i,j}$ is denoted as the $i_{th}$ data point in curve j, and $S_{i,j}$ as the $_{th}i$ data point in simulated curve j, then the fitting error for signal curve j is $$E_j = \sqrt{\sum_{i=1}^{n_j} \left( \frac{S_{i,j} - D_{i,j}}{D_{max,j}} \right)^2} \quad (M.2)$$

where $D_{max,j}$ is the maximum signal of signal curve. In this way, each experimental binding curve in the sensor array is compared to the binding curve predicted from the model. This error is then minimized to get the best fit and calculate $k_{on}$. The absolute error was denominated by the maximum signal of the signal curve, so the fitting error was a percentage of the signal level. Therefore, percentage based relative fitting errors for large signal curves were similar to that of small signal curves. The total fitting error is:

$$E = \sqrt{\sum_{j=1}^{N} E_j^2} \quad (M.3)$$

This total fitting error is minimized in the fitting of the kinetic data presented herein.

7. Traditional Two-Compartment Model

The binding kinetics of a ligand in solution to a capture agent on a surface may be modeled as a two-compartment reaction. This allows for both reaction and transport kinetics to be incorporated into models where the soluble ligand in the surface compartment reacts with the surface, via the chemical process of association and dissociation (see FIG. 2), and is gradually replenished by diffusion, flow, and convection from the bulk compartment. Within each compartment, the concentrations are assumed to be uniform in space, but they may change in time. The concentration of ligands in the bulk compartment, $C_0$, is assumed to be constant, while the ligand concentration in the surface compartment, $C_s$, is depleted due to the binding reaction, but is replenished by both diffusion of bulk ligand and by dissociation of surface bound complexes. This two-compartment reaction can be described as follows:

(M.4)

(M.5)

where $C_S$ and $C_0$ represent the solution concentration of magnetically tagged antibody in the surface and bulk compartments, R is the surface concentration of ligand or receptor immobilized on the surface (i.e., the surface density of available binding sites), n is the surface concentration of bound MNP-antibody-antigen complexes, $k_M$ is a diffusion-limited rate constant, $k_{on}$ and $k_{off}$ are the association and dissociation rate constants, respectively. The net reaction rates of $C_S$ and n can be defined by the following set of equations:

$$V\frac{dC_S}{dt} = Vk_M(C_0 - C_S) - Ak_{on}C_S R + Ak_{off}n \quad (M.6)$$

$$\frac{dn}{dt} = k_{on}C_S R - k_{off}n \quad (M.7)$$

Since kinetics was analyzed both in a volume and at a surface, R, n and $n_{max}$ are expressed in moles m$^{-2}$ whereas $C_S$ and $C_0$ are expressed in moles m$^{-3}$. By multiplying the solution rates by the volume of the surface compartment, V, and the surface rates by the area of the sensor, A, each equation can be presented in the same units (moles/s). The initial conditions at time t=0 are $C_S=C_0$ and n=0. During release measurements, all reactants are washed away so $C_0=0$.

Numerical methods may be used to solve Equation M.6. The experimental setup of surface plasmon resonance (SPR) limits simplification of the two-compartment model. With SPR, the soluble ligands are unlabeled (leading to rapid rates of diffusion) and they are introduced to the reaction surface under high flow rates. Therefore, the mass transport-limited rate constant, $k_M$, may play a major role in the kinetic interaction observed.

8. Modified Two-Compartment Model with Analytical Solution

In contrast to SPR instrumentation, embodiments of the single well GMR sensor system utilized labels to enhance the signal of molecular binding events and there was no deliberate flow during measurements. The size of the labels (e.g., 46 nm) and the absence of flow significantly reduced the rate of diffusion and convection of the soluble ligand between bulk and surface compartments. If the rate of diffusion is significantly slower than the rate of the reaction, it is possible to reduce the traditional two-compartment model to a modified form that can be solved analytically.

Figure 5A:
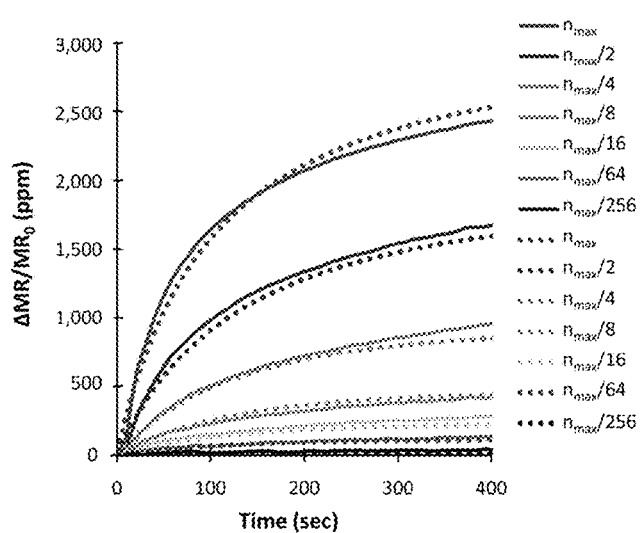
FIG. 5(a) shows a graph of binding curves of anti-EpCAM antibody to surface immobilized EpCAM antigen predicted by the analytical model (dotted lines) in Equation M.6 and measured experimental data (solid lines) when the surface concentration of EpCAM protein was diluted from 5 attomoles ($n_{max}$) down to 20 zeptomoles ($n_{max}/256$) in serial dilutions of 2×, according to embodiments of the present disclosure. The fitting error of all the curves in this experiment to the curves predicted by the model was $R^2=0.98$.

To validate this assumption, numerical methods were used to solve equations M.6 and M.7 to fit the real-time binding data of EpCAM (shown in FIG. 5(a)). The $k_M$ extracted for our magnetically labeled antibodies was approximately $1.0 \times 10^{-4}$ s$^{-1}$. Therefore, as shown in FIG. 13 and explained in the next paragraph, the contribution of the rates of association, dissociation (assuming $k_{off}$ is on the order of $1.0 \times 10^{-6}$ s$^{-1}$ for most antibodies), and diffusion can be plotted to establish the relative importance of each component in Equation M.6.

Figure 13:
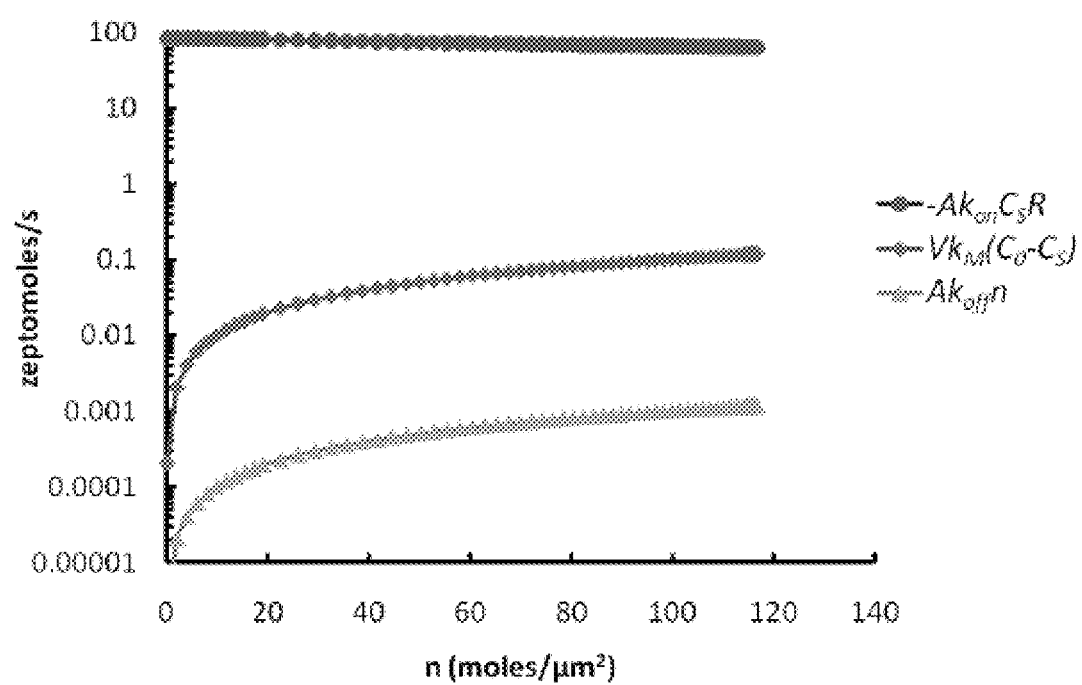
FIG. 13 shows a log-scale plot depicting the contribution of each term in Equation M.6 as a function of the number of magnetically labeled antibodies bound to the sensor surface, according to embodiments of the present disclosure.

From the rate equation M.6, each term at the right side of the equation was plotted as a function of the number of surface bound EpCAM antibody-antigen complexes, n (FIG. 13). The normalized MR signal (in ppm) was converted to n (in moles/μm$^2$) based on the relation that 150 surface bound MNPs produce 1 ppm of MR signal (see FIG. 7). Over the entire binding reaction, the association rate term remained orders of magnitude higher than both the dissociation rate and diffusion rate terms. Therefore, the magnetic nanoparticle labels were large enough to significantly slow the diffusion of magnetically labeled antibody into the surface compartment. This implies that regeneration of soluble antibody-MNP into the surface compartment was negligible (i.e. $k_M$~0). In addition, FIG. 13 showed that it was valid to assume that $k_{off}$ was negligible on the time scale of these binding experiments. However, as will be shown below, $k_{off}$ is not negligible in measurements of release kinetics.

FIG. 13 shows a log-scale plot depicting the contribution of each term in Equation M.6 as a function of the number of magnetically labeled antibodies bound to the sensor surface. The experimental data for EpCAM binding presented in FIG. 5(a) was used to numerically calculate the values of $k_{on}$, $k_{off}$, and $k_M$ for this graph. The x-axis represents the surface concentration of magnetically labeled antibody bound to the sensor surface throughout the binding reaction (n values in the plot were derived from real experimental data). At n=0, the experiment began and at n~120 moles/μm², the signal nearly reached saturation or the binding experiment ended. Over the entire binding reaction, the association rate term remained orders of magnitude higher than both the dissociation and diffusion rate terms. Therefore, it was valid to assume that $k_{off}$ was negligible (as the $k_{off}$ curve was far below the $k_{on}$ curve). In addition, the magnetic nanoparticle labels were large enough to allow only slow diffusion of magnetically labeled antibody into the reaction compartment (as the $k_M$ curve was far below the $k_{on}$ curve). This implied that delivery of soluble antibody-MNP into the surface compartment was negligible (i.e. $k_M$ was approximately zero).

Since the MNP-antibody in the surface compartment was not significantly replenished by slow diffusion from the bulk compartment, mass balance required that the concentration of un-reacted antibody-MNP in solution at the surface, $C_S$, be equal to the difference of the initial concentration, $C_0$, and the amount consumed in the formation of the product, nA, divided by the volume V, such that:

$$C_S = C_0 - n\frac{A}{V} \tag{M.8}$$

Similarly, mass balance requires the surface concentration of free binding sites, R, to be equal to the difference in its initial surface concentration $R_0$, and the amount consumed in formation of the MNP-antibody-antigen complexes. The magnitude of $R_0$ must be appreciably smaller than the maximum concentration of close packed MNPs on the surface to avoid avidity effects in which one MNP binds to multiple antigens. Therefore, $R_0$ was replaced with the maximum deposited surface concentration of antigen, $n_{max}$, as follows:

$$R = R_0 - n = n_{max} - n \tag{M.9}$$

Thus, Equation M.7 reduces to:

$$\frac{dn}{dt} = k_{on}\left(C_0 - n\frac{A}{V}\right)(n_{max} - n) \tag{M.10}$$

Here, the two terms within parentheses represent the depletion of tagged antibody in the surface compartment and reduction of available surface binding sites, respectively. Equation M.7 now has the following analytical solution:

$$n = n_{max}\left[\frac{1 - e^{-k_{on}(C_0 - n_{max}A/V)t}}{1 - \frac{n_{max}A}{C_0 V}e^{k_{on}(C_0 - n_{max}A/V)t}}\right] \tag{M.11}$$

Many analytically solvable kinetic models require that one of the reactants in the interaction remain in excess for an analytical solution to be derived. However, with the model presented in Equation M.11, both reactants may be significantly depleted during the binding process. The flexibility of this model enables a more generalizable set of experiments to be conducted without violating strict reaction conditions. Furthermore, most kinetic models require the system to reach equilibrium in order to determine the association rate constant. However, with the model presented herein, equilibrium does not have to be reached and the association rate constants could be determined in 5 minutes or less, well prior to saturation.

There are five parameters $k_{on}$, $C_0$, $n_{max}$, V, and A in the analytical model. Among them, $k_{on}$, V and A were fixed to be the same for all signal curves from the same receptor-analyte pair; while $n_{max}$ and $C_0$ will be different if surface concentration of analytes or solution concentration of antibody-MNP complexes is changed.

9. Analytical Model can Reduce to Langmuir Absorption

When $C_0V/A \gg n_{max}$, corresponding to negligible depletion of reactants in the surface compartment, Eq. M.10 reduces to:

$$\frac{dn}{dt} = k_{on}C_0(n_{max} - n) \tag{M.12}$$

And the analytical model reduces to the Langmuir model. Thus, Eq. M.11 reduces to:

$$n = C_0\frac{V}{A}\left[\frac{1 - e^{-k_{on}(A/V)(C_0(V/A) - n_{max})t}}{\frac{C_0V}{n_{max}A} - e^{-k_{on}(A/V)C_0(V/A - n_{max})t}}\right] \tag{M.13}$$

$$n = \cancel{C_0\frac{V}{A}}\left[\frac{1 - e^{-k_{on}(A/V)(C_0(V/A))t}}{\frac{\cancel{C_0V}}{n_{max}\cancel{A}}}\right]$$

$$n = n_{max}(1 - e^{-k_{on}C_0 t})$$

This result matches Langmuir binding kinetics, with the added assumption that $k_{off}$ is negligible. A comparison of our binding data to the Langmuir model is presented in FIG. 14. This reduced form of the analytical model, Equation M.13, is the same as the Langmuir isotherm derived below (Equations M.14-25) and presented in Equation M.25.

Figure 14:
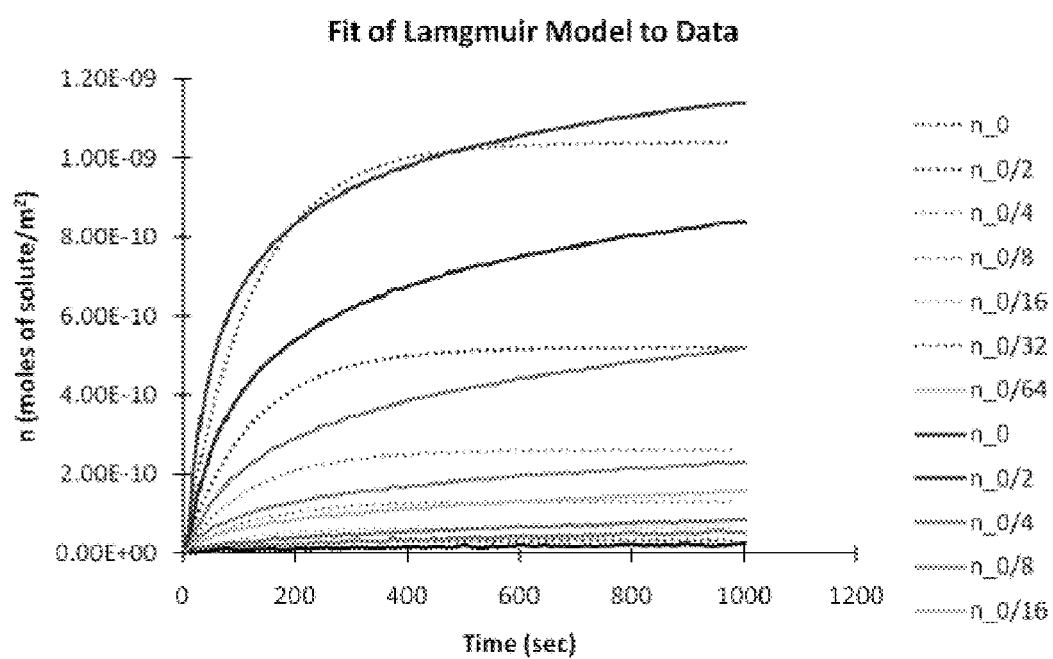
FIG. 14 shows a graph of binding curves of anti-EpCAM antibody to surface immobilized EpCAM antigen predicted by a Langmuir absorption model (dotted lines) and measured experimentally (solid lines), according to embodiments of the present disclosure.

FIG. 14 shows a graph of binding curves of anti-EpCAM antibody to surface immobilized EpCAM antigen predicted by a Langmuir absorption model (dotted lines) and measured experimentally (solid lines). The surface coverage of EpCAM protein was diluted from 5 attomoles (corresponding to $n_{max}$) down to 19.5 zeptomoles (corresponding to $n_{max}/256$) in serial dilutions of 2×. From the superimposed graphs, the Langmuir absorption model did not adequately describe the real time binding kinetics observed by embodiments of the GMR sensors for the set of concentrations tested. Therefore, a new model was derived in order to better describe the binding kinetics observed. The analytical model presented herein includes an additional term which accounts for both the rapid onset and slower persistent rises in signals.

The Langmuir isotherm relates the coverage or adsorption of molecules on a solid surface to concentration of the medium above the surface at a fixed temperature. The Langmuir equation can be derived considering surface ligands, L, suspended labeled molecules in the medium, C, and absorbed molecular complexes, CL, then the adsorption process can be represented as $$C+L \leftrightarrow CL \quad \text{(M.14)}$$

The association rate, $R_a$, and dissociation rate, $R_d$, are, respectively, $$R_a = k_{on}[C][L] \quad \text{(M.15)}$$

$$R_d = k_{off}[CL] \quad \text{(M.16)}$$

where $k_{on}$ and $k_{off}$ are association rate constant and dissociation rate constants, and square brackets denote concentrations.

If the total available ligand concentration is $[L_{max}]$, and the normalized surface coverage of absorbed molecule is $\theta$, then $$[L]+[CL]=[L_{max}] \quad \text{(M.17)}$$

$$\theta=[CL]/[L_{max}] \quad \text{(M.18)}$$

Thus, [L] is as follows:

$$[L]=(1-\theta)[L_{max}] \quad \text{(M.19)}$$

Substituting Equations M.19 and M.18 Back into Equations M.15 and M.16, respectively, gives the following:

$$R_a = k_{on}(1-\theta)[L_{max}][C] \quad \text{(M.20)}$$

$$R_d = k_{off}\theta[L_{max}] \quad \text{(M.21)}$$

Assuming that $k_{off}$ is negligible on the time scale of the experiment, and solving for $R_a$, gives:

$$R_a = \frac{d[CL]}{dt} = k_{on}(1-\theta)[L_{max}][C] \quad \text{(M.22)}$$

$$\frac{d[CL]}{dt} = k_{on}([L_{max}]-[CL])[C] \quad \text{(M.23)}$$

$$\int \frac{d[CL]}{[L_{max}]-[CL]} = \int k_{on}[C]dt \quad \text{(M.24)}$$

Assuming [C] is independent of time and $[L_{max}]$ is, independent of [CL] and solving via integration by parts, the solution is as follows:

$$[CL]=[L_{max}](1-e^{-k_{on}[C]t}) \quad \text{(M.25)}$$

10. Model of Release Kinetics:

Antibodies bind to their targets with very high affinity. Therefore, the dissociation rate constants are typically small requiring longer time periods (e.g., minutes) in order to observe such release phenomenon. In addition, due to the avidity of antibodies, the release kinetics were monitored using competitive inhibition. By placing high concentration of target in solution, a more accurate measurement of the release kinetics can be observed.

The rate equations for the rate of antibody release can be written as follows:

(M.26)

$$\frac{dn}{dt} = -k_{off}n \quad \text{(M.27)}$$

Therefore, the surface bound MNP-antibody concentration at time t after adding the release solution is:

$$n_{Release}(t) = n_{max}e^{-k_{off}t} \quad \text{(M.28)}$$

where $n_0$ is the initial absorbed MNP-antibody concentration at the sensor surface.

B. Results and Discussion

Provided is a method for measuring binding kinetics with arrays of individually-addressable, magnetically-responsive nanosensors to simultaneously monitor the kinetics of numerous distinct proteins, binding to their corresponding targets, which are immobilized on a sensor surface. These magneto-nanosensors were successfully scaled to over 1,000 sensors per 1 mm² chip area. Analyte epitope mapping was demonstrated and spatial dynamics of protein diffusion in solution was visualized. In conjunction with these experiments, an analytical kinetics model which accurately describes the real-time binding of labeled proteins to surface-immobilized proteins was derived. The analytical model had close agreement to similar experiments using surface plasmon resonance and data from the literature. This model may be applied for antibody-antigen binding at sensitivities of 20 zeptomoles ($20\times10^{-21}$) of solute or less.

1. GMR Sensors

Figure 4A:
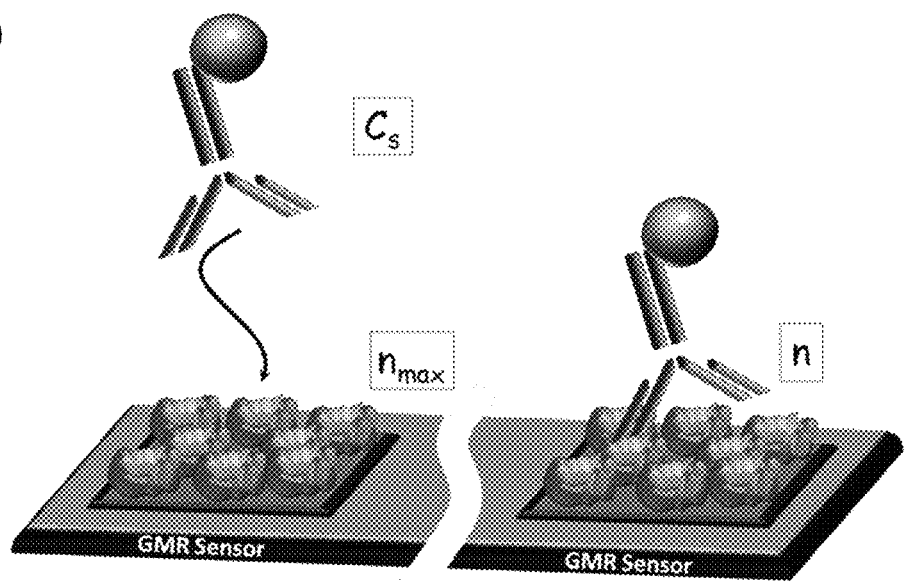
FIG. 4(a) shows a schematic representation of antibody-antigen binding (not drawn to scale), according to embodiments of the present disclosure. On the left, antibody labeled with a magnetic tag in solution at concentration $C_s$ approaches the GMR sensor surface. When not bound, the diffusing magnetically labeled antibody is too far from the GMR sensor to be detected. On the sensor surface is antigen, immobilized at an initial surface concentration of $n_{max}$. Once the magnetically labeled antibody binds to the antigen, as depicted on the right, the magnetic field from the magnetic tag is detected by the underlying proximity-based GMR sensor. The captured antibody-antigen complex is represented as n.

Soluble ligand was pre-labeled with a magnetic nanoparticle (MNP) in order to monitor the real-time binding kinetics of the ligand complex to antigen immobilized on the sensor surface (FIG. 4(a)). The magnetic field from the antibody-MNP complexes induced a change in electrical resistance in the underlying GMR sensor as the complexes were captured in real-time. Due to the rapid, real-time readout of the GMR sensor array, the kinetics of binding were monitored and quantified to determine the associated kinetic rate constants.

Figure 4B:
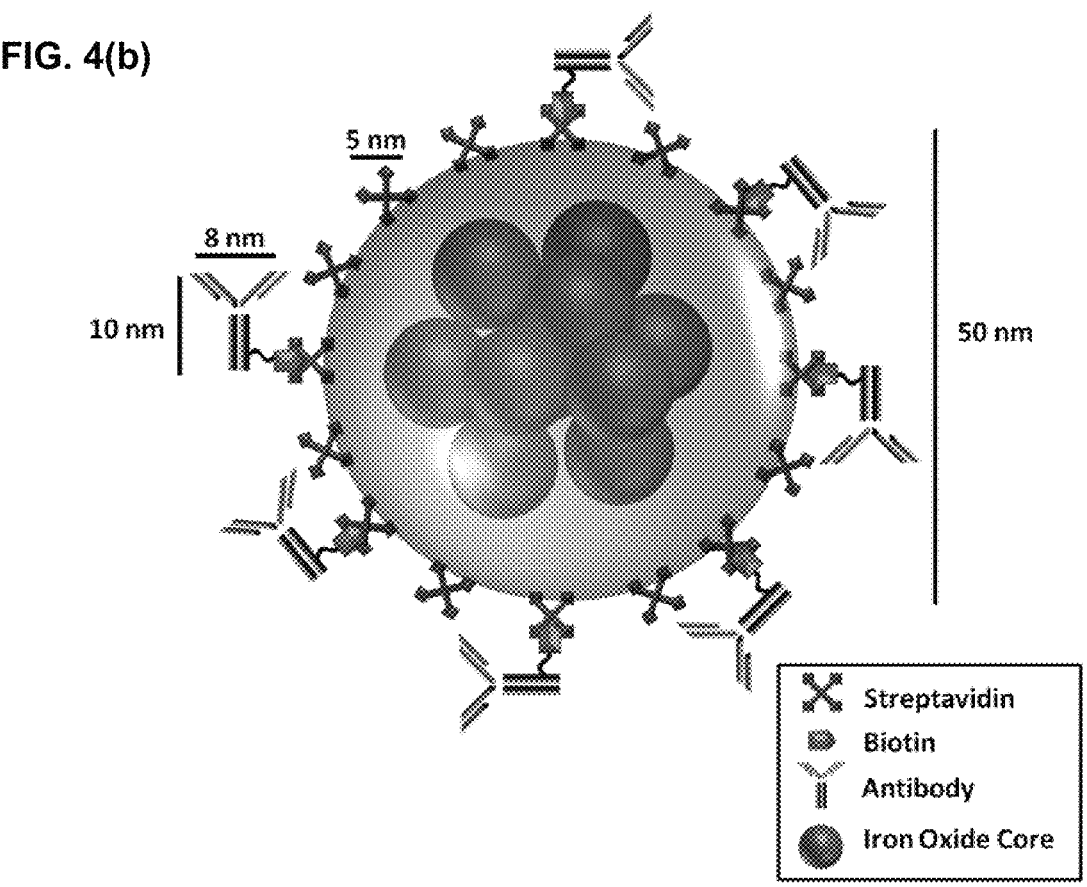
FIG. 4(b) shows a schematic representation of a magnetically labeled antibody drawn to scale, according to embodiments of the present disclosure. The magnetic tag includes several iron oxide cores embedded in a dextran polymer and then functionalized with antibody or receptor.

The MNPs which label the protein or antibody of interest were twelve 10 nm iron oxide cores embedded in a dextran polymer (FIG. 4(b)), as determined by TEM analysis. The entire nanoparticle averaged 46±13 nm in diameter (from number weighted Dynamic Light Scattering). Based on the Stokes-Einstein relation, these particles had a translational diffusion coefficient of approximately $8.56\times10^{-12}$ m² s⁻¹. The MNPs had a zeta potential of −11 mV. These particles were superparamagnetic and colloidally stable, so they did not aggregate or precipitate during the reaction. In addition, the GMR sensors operated as proximity-based detectors of the dipole fields from the magnetic tags; thus, only tags within 150 nm of the sensor surface were detected. Therefore, unbound MNP tags contributed negligible signal in the absence of binding. Only bound magnetically labeled antibodies will be detected by the underlying GMR sensor, making this MNP-GMR nanosensor system useful for real-time kinetic analysis.

Figure 4C:
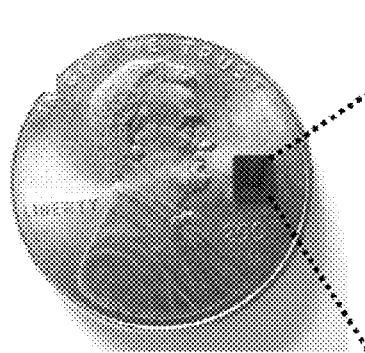
FIG. 4(c) shows a photograph of a 1 mm² die that includes 1,008 magnetic sensors, according to embodiments of the present disclosure.
Figure 4D:
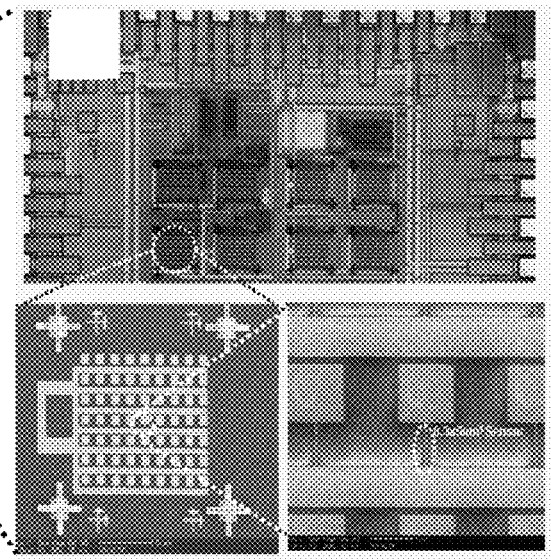
FIG. 4(d) show optical micrograph and scanning electron microscopy (SEM) images of a fully processed die, according to embodiments of the present disclosure. 1,008 GMR biosensors were divided into 16 subarrays, and each subarray occupied an area of 90 μm×90 μm.

A GMR sensor array was fabricated with 1,008 sensors on a 1 mm² chip area (FIG. 4(c)). The calculated feature density was over 100,000 GMR sensors per cm². The sensor array was designed as a set of sub-arrays, where each sub-array occupied an area of 90 µm×90 µm (FIG. 4(d)). The sensor array was compatible with robotic spotters. Each sensor within a sub-array was individually addressable by row and column decoders via a shared 6-bit control bus fabricated with VLSI technology. The GMR sensor arrays allowed for parallel multiplex monitoring of protein binding kinetics.

Another embodiment of the GMR sensor is shown in FIG. 12. In FIG. 12, 12 elongated linear magnetic sensor segments were connected together in parallel, and 6 groups of these parallel-connected segments were connected together in series, giving a magnetic sensor with a total of 72 magnetic sensor segments. The magnetic sensor was 100 µm×100 µm. Each magnetic sensor segment was 750 nm wide, 20 nm thick and 100 µm in length. The inset in FIG. 12 shows a SEM image of nanoparticles bound to a magnetic sensor segment.

2. Model of Binding Kinetics

As set forth above, an analytical model capable of fitting real-time binding kinetics data so that one can calculate the association rate constant ($k_{on}$) and the dissociation rate constant ($k_{off}$) was derived.

The binding reaction is a two-step process where the antibody in the bulk solution first approaches the surface captured antigen via diffusion and flow, and then binds to or escapes from the surface-bound target via the chemical processes of association and dissociation. If the antibody concentration of the bulk solution is spatially uniform, then $$C_S = C_0 - n\frac{A}{V} \quad (1)$$

where $C_s$ is the concentration of the magnetically tagged antibody at the surface of the sensor, $C_0$ is the initial bulk concentration of magnetically tagged antibody, and n is the surface concentration of bound MNP-antibody-antigen complexes. V is the volume of the solution above the sensor that is involved in the binding reaction and A is the reaction area (in this case the surface area of one sensor). Based on simple kinetics, the surface reaction is described as follows:

$$\frac{dn}{dt} = k_{on}\left(C_0 - n\frac{A}{V}\right)(n_{max} - n) - k_{off}n \quad (2)$$

The two terms within parentheses account for the reduction of bulk reactants and of available surface sites, respectively, $n_{max}$ is the concentration of potential binding sites on the sensor surface, $k_{on}$ is the association rate constant and $k_{off}$ is the dissociation rate constant for the binding reaction. As both volume and surface concentrations are discussed, n and $n_{max}$ are expressed in mole m$^{-2}$ whereas $C_s$ and $C_0$ are expressed in mole m$^{-3}$. Note that $n_{max}$ is limited by the maximum concentration of close packed MNPs, not by the maximum concentration of analyte on the surface. Therefore, in order to exclude steric effects related to MNP crowding on the sensor surfaces, the highest analyte surface concentration tested was at least 10 times lower than the surface concentration of the close packed antibody-MNP complexes.

This equation may be simplified by assuming that $k_{off}$ is zero, since the antibody-antigen dissociation is negligible on the time scale of the present experiments. Equation 2 now has the following analytical solution:

$$n = n_{max}\left[\frac{1 - e^{-k_{on}(C_0 - n_{max}A/V)t}}{1 - \frac{n_{max}A}{C_0V}e^{-k_{on}(C_0 - n_{max}A/V)t}}\right] \quad (3)$$

If $C_0V \gg n_{max}A$, which implies an excess of solution molecules over available surface sites, the kinetics follow Langmuir absorption. However, when this is not the case, the solution may be significantly depleted of reactants, particularly near the surface of the sensor, so the reaction rate will be slowed by the requirement for subsequent reactants to diffuse over a macroscopic distance (~V/A) before reacting (especially for labeled molecules). This characteristic diffusion distance, V/A, is taken into account in this kinetic model by defining the thickness of the fluid that is participating in the binding reaction, i.e. the compartment of the solution available to bind to the surface. Any solute above the characteristic V/A height may not contribute in the binding reaction in the relevant timeframe.

C. Experimental Results

To test this analytical solution, epithelial cell adhesion molecule (EpCAM) antibody-antigen binding kinetics were determined using the above model and the experimental results were compared to the literature.

Varying Concentration of Sensor-Bound Molecule

In the first set of experiments, presented in FIG. 5(a), a binding assay of MNP-labeled anti-EpCAM antibody to surface-bound EpCAM protein was performed. $C_0$, $n_{max}$, and V/A in the model were fixed values determined from dimensions and concentrations, and $k_{on}$ was determined by best fit of binding curves predicted by the kinetic model to experimental data. A binding assay of a fixed concentration of MNP-anti-EpCAM antibody to varying concentrations of surface bound EpCAM protein was performed. Two-fold dilutions were used to prepare a series of sensor surfaces; beginning at a loading mass (e.g., the amount of protein that was bound to the sensor surface and functional) of 5 attomoles of EpCAM protein and diluting sequentially down to 20 zeptomoles. The only parameter which varied between binding curves was $n_{max}$; all other parameters were unchanged. When implementing this one parameter change in the model, each experimental binding curve was fitted accurately (FIG. 5(a)). The values of the parameters were (the undiluted) $n_{max}$=9.5×10$^{-10}$ mol m$^{-2}$, $C_0$=6.8×10$^{-7}$ M, A=5.4×10$^{-9}$ m$^2$, and V=5.5×10$^{-12}$ m$^3$. Accordingly, $k_{on}$=2.5×10$^4$ M$^{-1}$ s$^{-1}$ fit the data best. The fitting error of all the curves in this experiment to the curves predicted by the model was R$^2$=0.98. In addition, after the MNP-antibody solution was washed away and replaced by antigen-loaded buffer, dissociation rate constants were calculated by fitting the subsequent data to a basic exponential decay model, $n_{Release}(t) = n_{max}e^{-k_{off}(t)}$, where $n_0$ is the surface concentration of bound MNPs at the time of washing. Accordingly, the anti-EpCAM antibody-antigen dissociation rate constant, $k_{off}$, was determined to be 2.0×10$^{-6}$ s$^{-1}$. This confirms the assumption above that $k_{off}$ was essentially negligible when compared to $k_{on}$.

Varying Concentration of Analyte in Assay Mixture

Figure 5B:
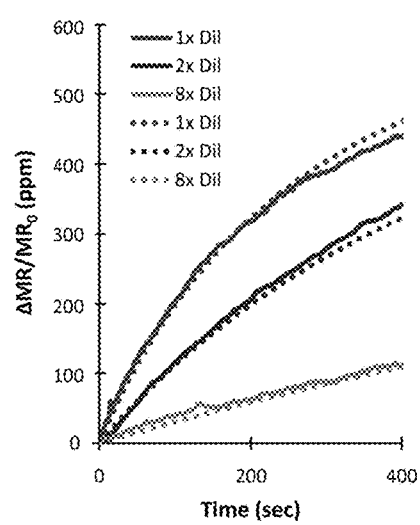
FIG. 5(b) shows graphs of binding curves of MNP-anti-EpCAM antibody to 833 zeptomoles ($n_{max}/6$) of EpCAM antigen immobilized on the sensor surface predicted by the analytical model (dotted lines) and measured experimental data (solid lines) when the solution concentration of MNP-anti-EpCAM protein was undiluted, diluted 2× and diluted 8×, according to embodiments of the present disclosure. The fitting error of all the curves to the model was $R^2=0.96$. The y-axis is presented as changes in MR normalized to the initial MR in parts per million (ppm).

In a second set of experiments, presented in FIG. 5(b), each sensor was immobilized with a constant load mass of 833 zeptomoles of EpCAM protein (⅙ of maximum amount used in FIG. 5a). The concentration of antibody-MNP complex applied to the sensors was varied between undiluted, twofold diluted and eightfold diluted solutions of antibody-MNP complexes (corresponding to $C_0$, $C_0/2$ and $C_0/8$ in the model). Since the antibody-antigen interaction remained the same whether $C_o$ was altered or $n_{max}$ was altered, the rate constants describing the interaction above remained the same across these experiments. In fitting the model, the same $k_{on}$ of 2.5×10$^4$ M$^{-1}$ s$^{-1}$ was obtained, supporting the validity of the analytical model. The fitting error of all the curves to the model was R$^2$=0.96. These results lie within the normal range reported in the literature, confirming the validity of the kinetic model to predict binding and the accuracy of the results derived (see Table 1).

Similar real-time experiments were performed in order to quantify MNP-anti-carcinoembryonic antigen (CEA) antibody to CEA, MNP-anti-vascular endothelial growth factor (VEGF) antibody to VEGF, and MNP-streptavidin to biotin binding kinetics (FIGS. 6(a) to 6(d)). For anti-CEA antibody, binding and dissociation rate constants were monitored on both GMR sensors and SPR instrument with the same reagents and results compared (FIGS. 6(c) and 6(d)).

Figure 6A:
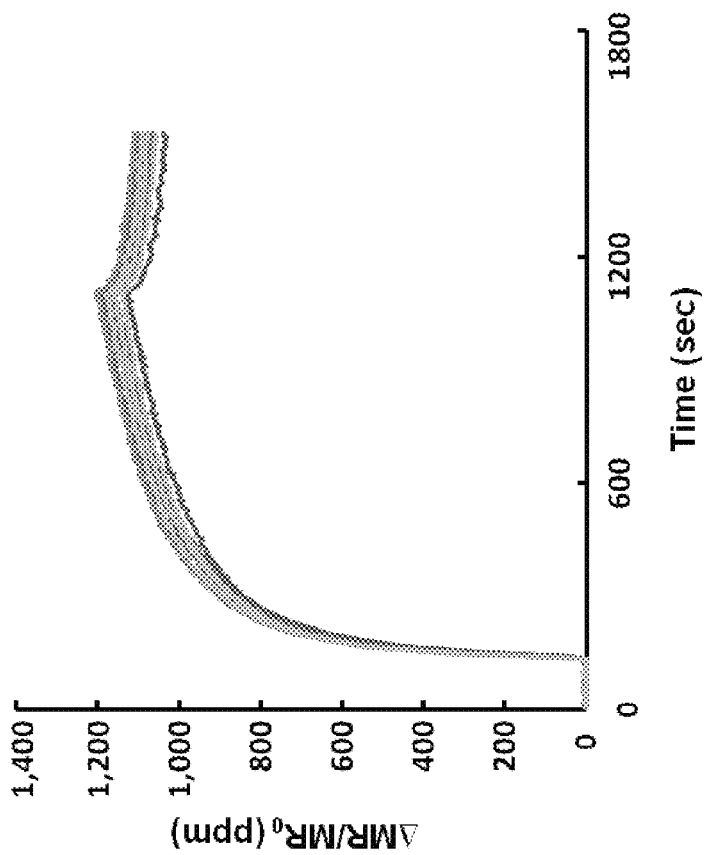
FIG. 6(a) shows graphs of multiplex kinetic analysis of anti-CEA antibody to antigen on 12 replica sensors and anti-VEGF antibody to antigen on 3 replica sensors, according to embodiments of the present disclosure.
Figure 6B:
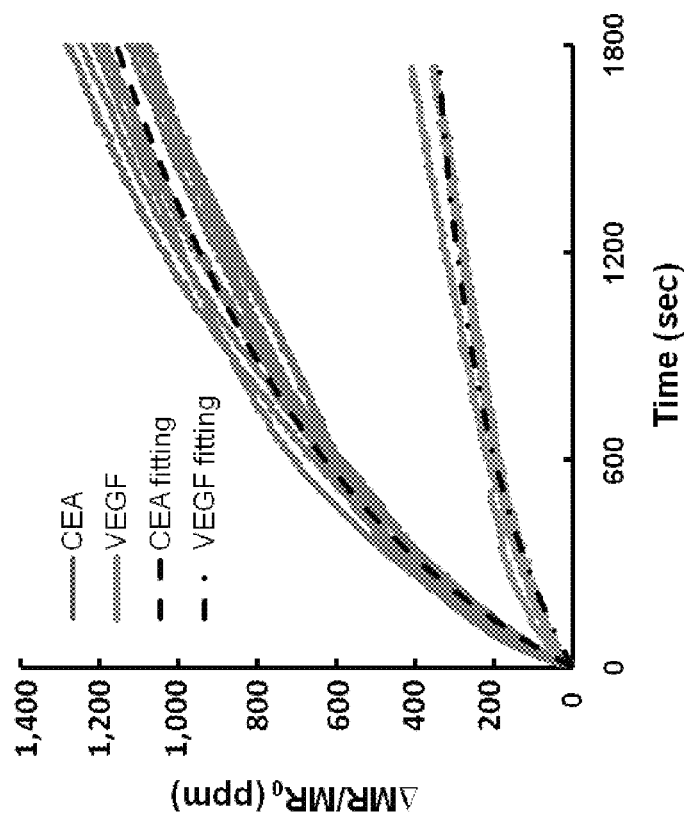
FIG. 6(b) shows a graph of 25 replica sensors monitoring biotin to streptavidin binding kinetics.

FIG. 6(a) shows graphs of multiplex kinetic analysis of anti-CEA antibody to antigen on 12 replica sensors and anti-VEGF antibody to antigen on 3 replica sensors. The CEA antibody-antigen $k_{on}$ was $3.3 \times 10^4$ $M^{-1}$ $s^{-1}$ with an average fitting error of 2.8% and the VEGF antibody-antigen $k_{on}$ was $1.6 \times 10^4$ $M^{-1}$ $s^{-1}$ with an average fitting error of 8.2%. FIG. 6(b) shows a graph of 25 replica sensors monitoring biotin to streptavidin binding kinetics. The $k_{on}$ was $4.67 \times 10^6$ $M^{-1}$ $s^{-1}$ with a fitting error of 1.6%. Release kinetics were also monitored using a competitive biotin assay. FIG. 6(c) shows a graph of SPR and FIG. 6(d) shows a graph of magnetonanosensor-based platforms that provide similar real-time binding curves when monitoring the kinetics of CEA antibody binding to CEA antigen in parallel experiments. The GMR biosensor provided a $k_{on}$ of $5.0 \times 10^4$ $M^{-1}$ $s^{-1}$ and $k_{off}$ of $4.4 \times 10^{-4}$ $s^{-1}$ while SPR experiments yielded a $k_{on}$ of $5.2 \times 10^4$ $M^{-1}$ $s^{-1}$ and $k_{off}$ of $3.03 \times 10^{-4}$ $s^{-1}$. The dynamic range of the SPR was less than two orders of magnitude, and the GMR sensor had a dynamic range of 4 orders of magnitude or more. The dynamic range of the GMR sensor can be increased further with higher solute concentrations. In FIG. 6(d), the initial 1000 seconds of the binding curves was used to extract the $k_{on}$ value in accordance with the analytical model.

The GMR sensor array and SPR measurements yielded kinetic rate constants that were consistent with one another and to the values reported in the literature (Table 1), indicating that the MNP labeling has substantially no effect on measured rate constants when using the analytical model presented herein.

TABLE 1

| | GMR sensor ($\times 10^4$ $M^{-1}$ $s^{-1}$) | SPR ($\times 10^4$ $M^{-1}$ $s^{-1}$) | Literature |
|---|---|---|---|
| Biotinylated DNA and streptavidin | 467 | 550 | 300-4500 |
| EpCAM antigen and antibody | 1.2 | N/A | 3.2-40 |
| CEA antigen and antibody | 3.3-5.0 | 4.4 | 3.7-11 |
| VEGF antigen and antibody | 1.6 | N/A | 0.5-7 |

Table 1 shows a comparison of association rate constants for biotin to streptavidin binding, EpCAM antigen to EpCAM antibody, CEA antigen to CEA antibody, and VEGF antigen to VEGF antibody when using the GMR sensor array and SPR. For both SPR and GMR sensor experiments, the same antibody pairs were used. Both methods of kinetic analysis were consistent with the literature.

Quantification of the Number of Magnetic Tags Bound to a Sensor

Figure 7:
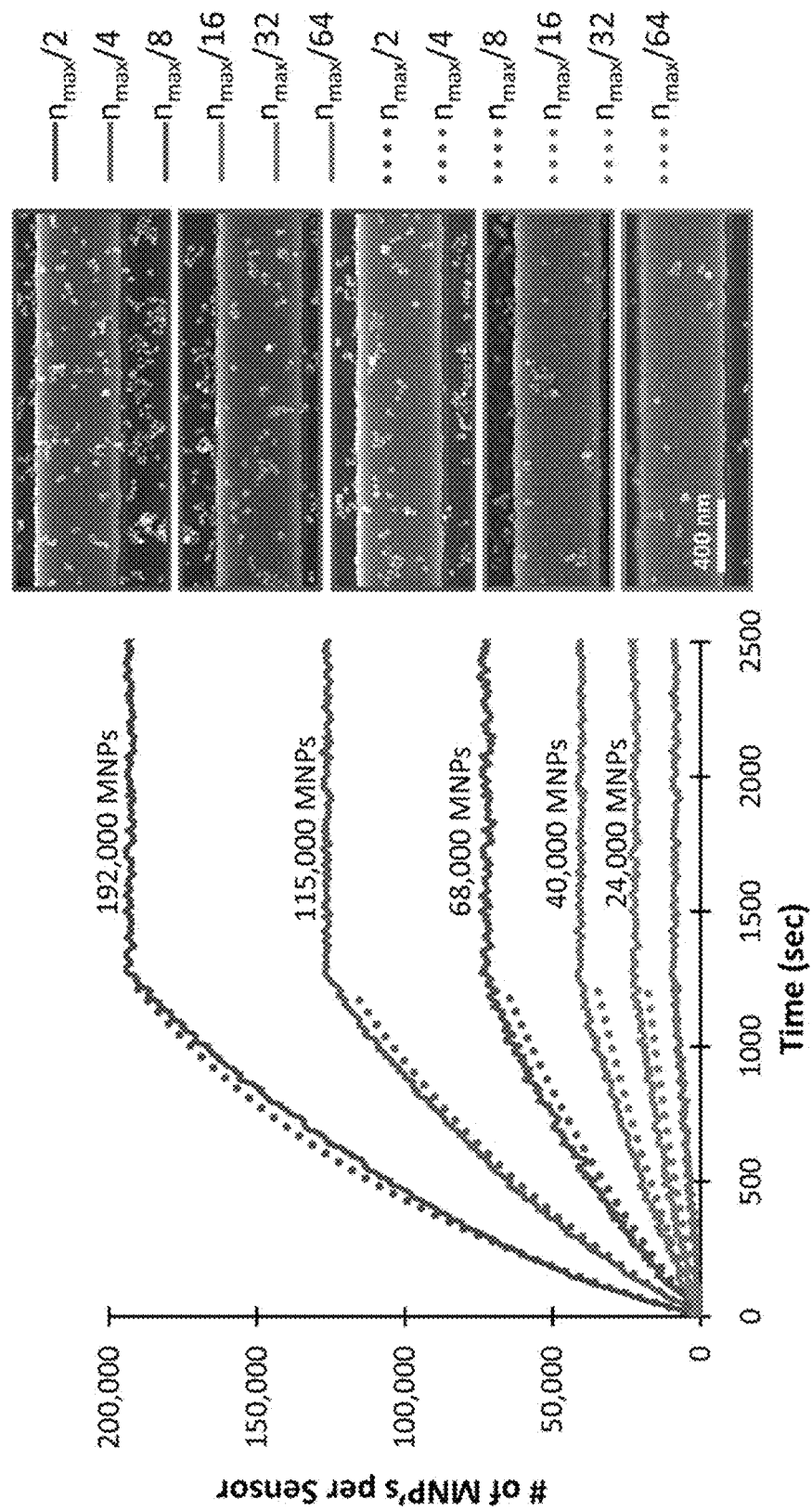
FIG. 7 shows a graph of the number of magnetic tags per sensor over time, according to embodiments of the present disclosure. SEM images for each of the loading masses (shown on the right of FIG. 7) were obtained to compare the number of MNPs bound in the experiment to that predicted by the model.

Scanning electron microscopy (SEM) confirmed that the analytical system was able to quantify the number of proteins captured on each sensor. Thus, by calibrating the GMR signal to an absolute number of magnetic tags bound to the sensor surface, the mass of protein bound and the signal generated per MNP was derived. For example, EpCAM protein was serially diluted in two fold increments starting at 2.5 attomoles down to 78 zeptomoles, on three to eight replica sensors. A 20-fold dilution of the MNP-antibody complexes was added to all the sensors and the binding kinetics were monitored. After 20 minutes of incubation time, the solution of magnetically labeled antibody was washed away, terminating the binding reaction, at which point the sensors with each surface concentration were imaged via SEM (FIG. 7). By normalizing the real-time experimental data and fitting it to the model, the sensor signal, measured as a change in MR normalized to the initial MR ($\Delta MR/MR_0$), was converted into the number of magnetic tags bound to each sensor. For example, the sensor functionalized with 2.5 attomoles of EpCAM protein captured 192,000 magnetic tags within the time of the experiment. SEM imaging showed that the experimental results matched with the kinetic model. Thus, the kinetic model may be used to quantify the number of tags bound per sensor and the number of proteins that bind during a given reaction.

Using the model, every 150 MNPs produce 1 ppm of signal. The lower limit of detection (LOD) of the sensors is approximately 20 ppm (defined by the average background signal of a non-complementary antibody coated sensor plus two standard deviations). Therefore, 0.6 particles/$\mu m^2$ or less can be detected.

Figure 8:
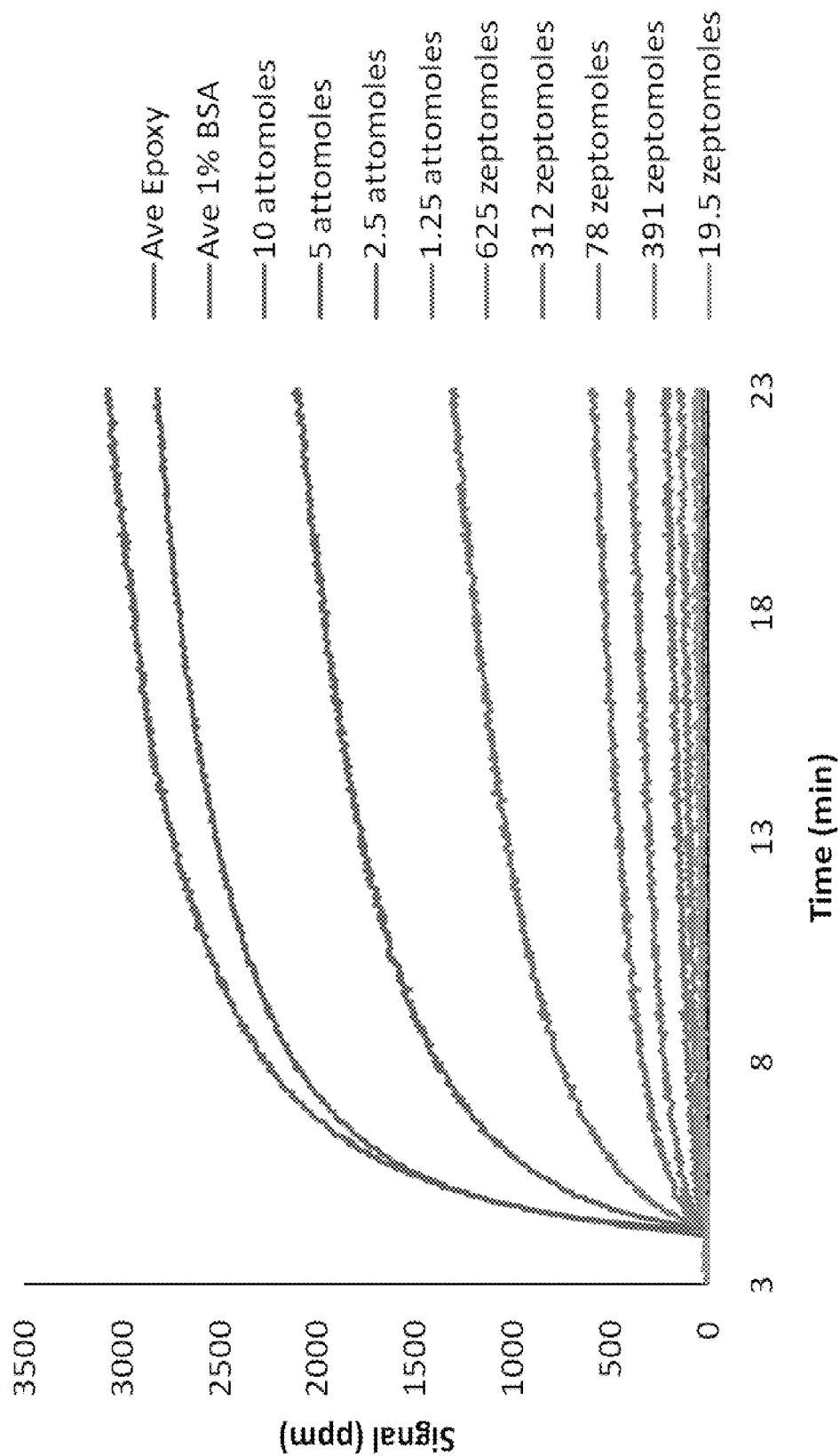
FIG. 8 shows a graph of sensor signals for varied immobilized antigen loadings over time, according to embodiments of the present disclosure.

In addition, the model was capable of explaining when saturation of the sensor surface will occur. As the loading mass of analyte was increased such that the surface concentration of protein approached that of the maximum MACS concentration on the sensor surface, a saturation in the signal was observed. This saturation occurred at a loading mass of 5 attomoles or more. The loading mass was calculated by depositing a known concentration and volume of protein on the sensor surface. After washing away the unreacted protein, the amount of bound protein was labeled with a nanoparticle. Via scanning electron microscopy, the number of active and bound proteins was quantified. At a loading mass of 5 attomoles or more, inter-nanoparticle steric effects became apparent. In all the experiments, 5 attomoles or less of loading mass was used. When a low protein concentration was deposited on the sensor surface, the distance between bound proteins on the sensor surface will be more than 1 MNP diameter apart, thereby preventing each nanoparticle from binding to more than one antigen. For example, at 5 attomoles, the highest loading mass tested, the average distance between proteins on the sensor surface was approximately 60 nm. Since the MNPs were only 46 nm in diameter, it was highly unlikely for a single MNP to bind to more than a single bound protein at the same time. Therefore, avidity (e.g., the combined strength of multiple binding interactions between two or more molecules) is substantially negligible. For example, when 10 attomoles of protein were deposited on the sensor surface, it appeared experimentally that the sensor surface was approaching saturation when compared to signals at 5 attomoles and lower (FIG. 8). A loading mass of 10 attomoles was described by the model as $n_{max}$ equal to $1.95 \times 10^{-9}$ mol m$^{-2}$. When this saturation value predicted by the model was compared to the physical limits of the sensor and the geometry of close packed MNPs, the values were in close agreement. The maximum surface concentration of protein constrained by the size of the MNPs in a single layer was $1.0 \times 10^{-9}$ mole m$^{-2}$.

Epitope Mapping

Epitope mapping experiments were performed using the real time binding assay and kinetic model disclosed herein. A set of different anti-EpCAM monoclonal antibodies was immobilized to GMR sensors. Sensors functionalized with anti-EGFR antibody were included as internal controls. EpCAM was then added in solution and captured in a unique configuration over each capture antibody. Subsequently, EGFR protein was added. If the captured EpCAM exposed an EGF-like repeat, then EGFR was able to bind. If however, the captured EpCAM protein was oriented in such a way to mask the EGF-like repeat, then EGFR was not able to bind (FIG. 9(a)).

FIG. 9(b) shows that anti-EpCAM antibody #1 bound the EpCAM protein to reveal the EGF-like domain; however, the EpCAM-anti-EpCAM antibody #2 complex hid the EGF-like domain. The anti-EpCAM Ab #1 sensor and anti-EpCAM Ab #2 sensors were functionalized with monoclonal anti-EpCAM antibodies specific to unique epitopes of EpCAM. When EpCAM bound to anti-EpCAM antibody #1, the EGF-like domain was exposed and the anti-EGFR antibody-MNP complex was able to bind. When the captured EpCAM protein bound to anti-EpCAM antibody #2, however, the EGF-like domain was not exposed and no binding took place.

When normalizing the binding curves of the anti-EGFR antibody-MNP complex to EGFR protein captured by EpCAM or EGFR capture antibodies, the kinetics of binding were the same as noted in the normalized binding curve (FIG. 9(c)). Even though the configuration of the macromolecular structures on each sensor was different, the kinetic interaction was the same. In FIG. 9(c), the binding curves were normalized. Since the two curves followed the same binding trajectory, the kinetic interaction involved in these two experiments was the same.

Spatial and Temporal Monitoring of Molecular Binding Interactions

Figure 10:
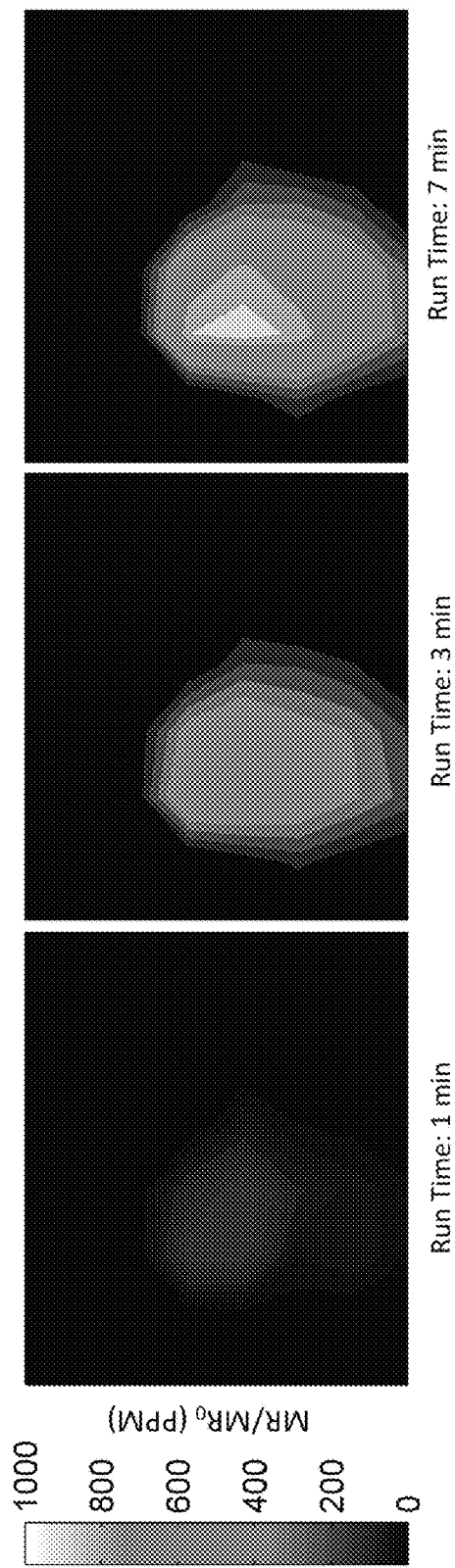
FIG. 10 shows a visualization of protein diffusion kinetics in 2D space at different times using a high density GMR sensor array, according to embodiments of the present disclosure. The units of the y-axis are presented in changes in MR normalized to the initial MR in parts per million (ppm).
Figure 11:
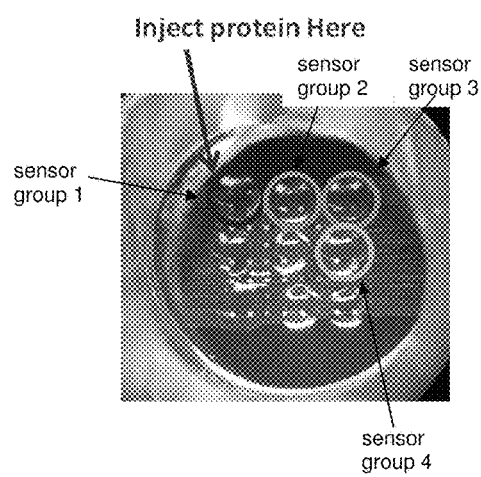
FIG. 11(a) shows a photograph of an experimental set up to monitor protein diffusion dynamics across a chip array using groups of magnetic sensors, according to embodiments of the present disclosure.
FIG. 11(b) shows graphs of the change in signal over time, according to embodiments of the present disclosure. Upon addition of soluble CEA antigen in the upper left corner of the well, it was possible to visualize the movement of CEA protein across the well in both space and time.
Figure 11B:
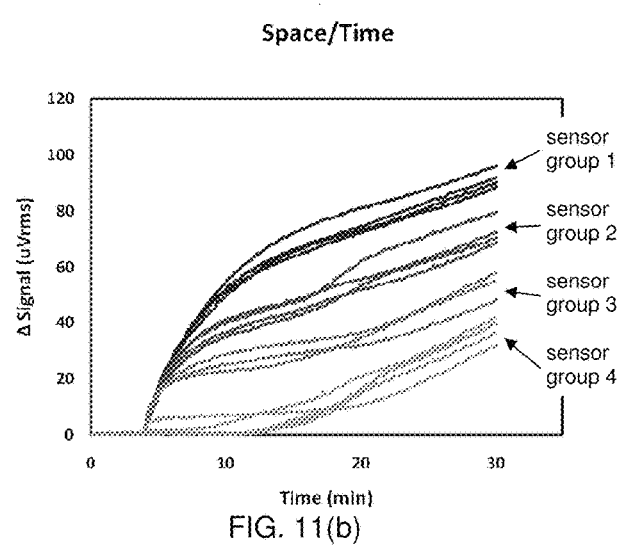

Another experiment using the real time binding assay was to monitor protein binding events both in space (due to the high density of the array architecture) and time (due to the rapid and real-time readout). Monoclonal anti-CEA capture antibody was attached across the sensor array. The magnetic tags labeled with anti-CEA antibody in solution were incubated above the sensor array prior to delivery of the CEA antigen protein. CEA antigen was injected onto the array, and the diffusion of CEA antigen across the array was monitored as the magnetically labeled detection antibody bound to the captured CEA antigen protein. Binding of CEA antigen protein to the sensor surface and then subsequent binding of magnetically labeled antibody resulted in MR signal changes across the spatially distributed sensors. The binding of CEA antigen to the sensor was visualized by observing the MNP-anti-CEA antibody binding kinetics to the sensor-bound CEA antigen (FIG. 10 and FIGS. 11(a) and 11(b)). The signal change over time was detected for four groups of four magnetic sensors (FIGS. 11(a) and 11(b)). Protein binding events, protein diffusion, and protein dynamics were analyzed with high spatial and temporal resolution. Transport parameters, such as diffusivity of the injected protein, may be derived by fitting the time course of MR signal at various sensor sites with a protein diffusion model.

The experimental results showed that the real time magnetic sensor device as disclosed herein was a high throughput, highly sensitive, real-time binding assay for detecting protein-protein interactions. The kinetic model derived above provided an analytical model of the dominant processes involved in labeled protein-protein interactions. The real time molecular binding assay and analytical model was used to measure protein binding rate constants and accurately quantify the number of proteins bound to a given sensor. Protein epitope mapping experiments and protein diffusion experiments were also performed.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of quantitatively determining a binding kinetic parameter of a molecular binding interaction, the method comprising:
producing a magnetic sensor device comprising a magnetic sensor comprising a spin valve sensor or a magnetic tunnel junction sensor in contact with an assay mixture comprising a magnetically labeled molecule suspended in a solution to produce a detectable molecular binding interaction, wherein the magnetic sensor comprises a molecule that specifically binds to the magnetically labeled molecule;
obtaining a real-time signal from the magnetic sensor without washing non-specific magnetic labels from the magnetic sensor; and
quantitatively determining with a quantitative analysis module of the magnetic sensor device a binding kinetic parameter of the molecular binding interaction from the real-time signal, wherein the quantitatively determining comprises processing the real-time signal with a two-compartment fitting algorithm.

2. The method according to claim 1, wherein the binding kinetic parameter is an association rate constant ($k_a$).

3. The method according to claim 1, wherein the binding kinetic parameter is a dissociation rate constant ($k_d$).

4. The method according to claim 1, wherein the binding kinetic parameter is a diffusion-limited rate constant ($k_M$).

5. The method according to claim 1, wherein the producing comprises applying the magnetically labeled molecule to the magnetic sensor.

6. The method according to claim 1, wherein the magnetic sensor comprises a capture probe that specifically binds to a molecule that specifically binds to the magnetically labeled molecule, and the producing comprises sequentially applying the molecule that specifically binds to the magnetically labeled molecule and the magnetically labeled molecule to the magnetic sensor.

7. The method according to claim 1, wherein the magnetic sensor comprises a capture probe that specifically binds to a molecule that specifically binds to the magnetically labeled molecule, and the producing comprises producing a reaction mixture comprising the molecule that specifically binds to the magnetically labeled molecule and then applying the reaction mixture to the magnetic sensor.

8. The method according to claim 1, wherein the molecular binding interaction is a binding interaction selected from the group consisting of a nucleic acid hybridization interaction, a protein-protein interaction, a receptor-ligand interaction, an enzyme-substrate interaction, and a protein-nucleic acid interaction.

9. The method according to claim 1, wherein the two-compartment fitting algorithm includes a bulk compartment and a surface compartment.

10. A method of quantitatively determining a binding kinetic parameter of two or more distinct molecular binding interactions, wherein each distinct molecular binding interaction includes a different magnetically labeled molecule, the method comprising:
producing a magnetic sensor device comprising two or more distinct magnetic sensors each comprising a spin valve sensor or a magnetic tunnel junction sensor each in contact with an assay mixture comprising a magnetically labeled molecule suspended in a solution to produce two or more distinct molecular binding interactions, wherein each magnetic sensor comprises a molecule that specifically binds to the magnetically labeled molecule;
obtaining a real-time signal from each magnetic sensor without washing non-specific magnetic labels from the magnetic sensors; and
quantitatively determining with a quantitative analysis module of the magnetic sensor device a binding kinetic parameter for each of the two or more distinct molecular binding interactions from the real-time signal, wherein the quantitatively determining comprises processing the real-time signal with a two-compartment fitting algorithm.

11. The method according to claim 10, wherein the binding kinetic parameter is an association rate constant ($k_a$).

12. The method according to claim 10, wherein the binding kinetic parameter is a dissociation rate constant ($k_d$).

13. The method according to claim 10, wherein the binding kinetic parameter is a diffusion-limited rate constant ($k_M$).

14. The method according to claim 10, wherein the binding interactions are binding interactions selected from the group consisting of nucleic acid hybridization interactions, protein-protein interactions, receptor-ligand interactions, enzyme-substrate interactions, and protein-nucleic acid interactions.

15. The method according to claim 1, wherein the magnetic sensor comprises a passivation layer having a thickness of 50 nm or less.

16. The method according to claim 1, wherein the magnetic nanoparticle comprises a surfactant.

17. The method according to claim 9, wherein a change in concentration of the magnetically labeled molecule in the surface compartment is described by the equation:

$$dC_S/dt = k_M(C_0 - C_S) - k_a C_S(B_{max} - B) + k_d B$$

wherein $k_M$ is a diffusion-limited rate constant, $C_0$ is a concentration of the magnetically labelled molecule in the bulk compartment, $C_S$ is a concentration of the magnetically labelled molecule in the surface compartment, $k_a$ is an association rate constant, $B_{max}$ is an initial available receptor concentration, B is a concentration of conjugate bound to the magnetic sensor, and $k_d$ is a dissociation rate constant.

18. The method according to claim 9, wherein a change in concentration of the molecular binding interaction is described by the equation:

$$dB/dt = k_a C_S(B_{max} - B) - k_d B$$

wherein $k_a$ is an association rate constant, $C_S$ is a concentration of the magnetically labelled molecule in the surface compartment, $B_{max}$ is an initial available receptor concentration, B is a concentration of conjugate bound to the magnetic sensor, and $k_d$ is a dissociation rate constant.

* * * * *

UNITED STATES PATENT AND TRADEMARK OFFICE
CERTIFICATE OF CORRECTION

PATENT NO. : 10,101,299 B2  
APPLICATION NO. : 13/046368  
DATED : October 16, 2018  
INVENTOR(S) : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1789 days.

Signed and Sealed this  
Twenty-seventh Day of August, 2019

Andrei Iancu  
*Director of the United States Patent and Trademark Office*